United States Patent
Lim et al.

(10) Patent No.: US 12,186,408 B2
(45) Date of Patent: Jan. 7, 2025

(54) FUSION POLYPEPTIDES FOR INHIBITING ANGIOGENESIS, FUSION PROTEIN NANOCAGES HAVING MULTIVALENT PEPTIDES FOR INHIBITING ANGIOGENESIS, AND THERANOSTIC USE THEREOF

(71) Applicant: INDUSTRY-UNIVERSITY COOPERATION FOUNDATION HANYANG UNIVERSITY ERICA CAMPUS, Gyeonggi-do (KR)

(72) Inventors: Dong Woo Lim, Seoul (KR); Min Jung Kang, Gyeonggi-do (KR)

(73) Assignee: Industry-University Cooperation Foundation Hanyang University Erica Campus, Gyeonggi-Do (KR)

( * ) Notice: Subject to any disclaimer, the term of this patent is extended or adjusted under 35 U.S.C. 154(b) by 705 days.

(21) Appl. No.: 17/604,414

(22) PCT Filed: Apr. 17, 2020

(86) PCT No.: PCT/KR2020/005176
§ 371 (c)(1),
(2) Date: Oct. 16, 2021

(87) PCT Pub. No.: WO2020/213993
PCT Pub. Date: Oct. 22, 2020

(65) Prior Publication Data
US 2022/0331453 A1   Oct. 20, 2022

(30) Foreign Application Priority Data

Apr. 18, 2019   (KR) .................. 10-2019-0045484
Apr. 17, 2020   (KR) .................. 10-2020-0046920

(51) Int. Cl.
*A61K 49/00*   (2006.01)
*A61K 38/00*   (2006.01)
*A61P 9/00*    (2006.01)
*C07K 14/435*  (2006.01)

(52) U.S. Cl.
CPC .......... *A61K 49/0054* (2013.01); *A61P 9/00* (2018.01); *C07K 14/435* (2013.01); *A61K 38/00* (2013.01); *A61K 49/0056* (2013.01); *C07K 2319/00* (2013.01)

(58) Field of Classification Search
CPC ............ A61K 49/0054; A61K 38/00; A61K 49/0056; A61K 9/51; A61P 9/00; C07K 14/435; C07K 2319/00; C07K 14/811; C07K 2319/735; C07K 2319/75; C07K 14/78; C07K 16/28; G01N 33/543
See application file for complete search history.

(56) References Cited

FOREIGN PATENT DOCUMENTS

| KR | 20060056582 | 5/2006 | |
| KR | 20120094867 | 8/2012 | |
| KR | 101296329 | 8/2013 | |
| KR | 20170115929 | 10/2017 | |
| KR | 101906494 | 12/2018 | |
| WO | WO2003038130 | * 5/2003 | ............... C12Q 1/68 |
| WO | 2016048246 | 3/2016 | |

OTHER PUBLICATIONS

Choi et al., "The incorporation of GALA peptide into a protein cage for an acid-inducible molecular switch," Biomaterials, 2010, vol. 31, pp. 5191-5198.
Kang et al., "Genetically Engineered Fusion Protein Nanocages for Nanomedicine Applications," 121st General Meeting of the Korean Chemical Society, 2018, abstract only.
WIPO, International Search Report for PCT/KR2020/005176, Aug. 18, 2020.
Kang et al., "Genetically Engineered Fusion Proteins for Anti-angiogenesis," The Polymer Society of Korea, Annual Spring Meeting, Apr. 2019.
Basheer, "1PS-287: Genetically Engineered Polypeptide-based Nanostructures for Theragnosis," The Polymer Society of Korea, Annual Fall Meeting, 2018, vol. 43, No. 2, 5 pages.

* cited by examiner

*Primary Examiner* — Marcela M Cordero Garcia
(74) *Attorney, Agent, or Firm* — Hodgson Russ LLP

(57) ABSTRACT

The present invention provides fusion polypeptides for inhibiting angiogenesis, fusion protein nanocages having peptides for inhibiting angiogenesis, and diagnostic and therapeutic (theranostic) uses thereof.

15 Claims, 6 Drawing Sheets
Specification includes a Sequence Listing.

(A) Anti-Flf1 peptide: GNQWFI
PEDF 34-mer: DPFFKVPVNKLAAAVSNFGYDLYRVRSSTSPTTN
EBPP[$A_1G_4I_1$]$_1$: VPAGG VPAAG VPAGG VPAGG VPAIG VPAGG

FUSION POLYPEPTIDES FOR INHIBITING ANGIOGENESIS, FUSION PROTEIN NANOCAGES HAVING MULTIVALENT PEPTIDES FOR INHIBITING ANGIOGENESIS, AND THERANOSTIC USE THEREOF

CROSS-REFERENCE TO RELATED APPLICATIONS

This application is a U.S. national stage entry of International Application No. PCT/KR2020/005176, filed Apr. 17, 2020, which claims priority to Korean Application No. 10-2019-0045484, filed Apr. 18, 2019, and Korean Application No. 10-2020-0046920, filed Apr. 17, 2020, the entire disclosures of which are incorporated herein by reference.

TECHNICAL FIELD

The present disclosure relates to a fusion polypeptide for inhibiting angiogenesis, a fusion protein nanocage having the peptide for inhibiting angiogenesis, and diagnostic and therapeutic (theranostic) uses thereof.

SEQUENCE LISTING

The instant application contains a Sequence Listing which has been submitted electronically in ASCII format and is hereby incorporated by reference in its entirety. Said ASCII copy, created on May 29, 2022, is named "083972_00018_SEQ_ID_ST25.txt", and is 32,276 bytes in size.

BACKGROUND ART

The proteins of organisms self-assemble into well-ordered structures to exert biological functions. The self-assembled structures and their biomedical applications are being studied actively. The well-ordered protein structures play important roles in cells and organisms such as genome packaging, structural support, storage and transportation of biological components, etc. The self-assembled structures are formed from bottom-up assembly of protein subunits, and have various structures such as nanofiber, ring-like and cage structures. Proteins that form these structures have been researched and developed in the field of biomedical applications as inherent structures or materials. An example of the well-ordered proteins are linear proteins such as collagen, amyloids and tubulin, which form nanofiber structures. The linear proteins such as collagen are prepared into films, sheets or hydrogels for drug delivery systems. The collagen film or sheet coats or transports a drug through chemical conjugation or physical entrapment for control of drug release. Fibrous proteins such as tubulin are fused with biotin to immobilize protein structures on target surface or work together with antibodies to transport a target protein. Other well-ordered proteins are ring-like proteins such as β-clamp or TRAP (trp RNA-binding attenuation protein). The function of these ring-like proteins is related with unwinding into single-stranded DNA, unwinding of supercoiled DNA, DNA transport or DNA manipulation by binding to DNA or RNA. Other protein structures are closed shell structures of cage proteins such as ferritin or viral capsids. The hollow space of the cage structures is used as used as microreactors or drug delivery carriers and functional peptides such as receptors are fused to the external shell. These protein structures are developed for advanced drug delivery systems via fusion with fluorescent dyes, other functional peptides such as drugs or chemicals.

The protein-based structures are advantageous in biomedical applications in that they are biocompatible and biodegradable. One of those protein structures is ferritin. It is a self-assembled nanocage structure formed by four helical bundles and relatively short helices. Ferritin is a member of a family of iron storage proteins in organisms and has a reversible pH responsiveness. Ferritin is degraded under strongly acidic conditions (pH 2) and is assembled again under neutral pH conditions. The reversible pH responsiveness of ferritin is utilized in several applications and in the construction of new chimeric proteins. For example, when ferritin is chemically conjugated with two different fluorescent dyes, the two dye-conjugated ferritins are mixed and degraded as pH is decreased. Thereafter, the pH is adjusted to natural pH for restoration to the original cage structures. The ferritin hybrid units labeled with different dyes are used as probes together with FRET (fluorescence resonance energy transfer) for distinction of signals from ferritin and degraded molecules. Another major feature of ferritin is the iron storage function. Ferritin is an iron storage protein in organisms. It was verified through many previous researches that ferritin stores metal ions including gold, lead, copper, etc. Specific amino acids have binding specificity in the cavity of the ferritin structure and amino acid sequences vary depending on the ions. For example, gold ion ($Au^{3+}$) is coordinated with Cys48, His49, Met96, His114 and Cys126, and lead ion ($Pd^{2+}$) is accumulated at the center of Glu45, Cys48, Arg52, Glu53 and His173. The accumulated metal ions are reduced to metal nanoparticles in the cavity of the cage structure, and the ferritin-metal nanoparticle composite has been used as a catalyst or an imaging probe for MRI (magnetic resonance imaging) or PET (positron emission tomography). For investigation of additional functions of ferritin, ferritin fragments have been replaced with other functional peptides or proteins, or they have been introduced to the outwardly exposed surface of ferritin. For example, a pH-responsive peptide or a cell-targeting peptide has been fused with ferritin by genetic engineering techniques. Despite the pH responsiveness of ferritin, the GALA peptide has been used to replace the short helix at the C-terminal as a pH-responsive peptide because the pH range (pH 2) is in extreme conditions. The GALA peptide exists as a random coil in neutral pH conditions. Under acidic conditions (pH 6), the cage structure is degraded due to conformational change into a helical structure. Other functional peptides have been introduced to two exposed parts of ferritin; they are the fourth helical bundle and a short helix at the N-terminal. In a previous study, the interleukin-4 receptor (IL-4R)-targeting peptide (AP-1) has been fused with the fourth helical bundle and the short helix of ferritin by a genetic engineering technique, and the binding and internalization of the fused ferritin to the IL-4R-expressing cell line, A549, have been reported. Ferritin has also been fused with RGD-4C, which binds to αVβ3 that positively feeds back with a tumor vasculature, as another cell-specific target peptide by a genetic engineering technique. The cell-specific targeting capacity of RGD-4C fused with ferritin has also been confirmed for melanoma cells.

Elastin is a key protein component of the extracellular matrix (ECM). It consists of an elastomeric domain and a crosslinking domain. The elastomeric domain consists of hydrophobic amino acids and alternating peptides such as VPGG (SEQ ID NO 23), VPGVG (SEQ ID NO 24) and APGVGV (SEQ ID NO 25). Elastin-based polypeptides (EBPs) are heat-responsive biopolymers derived from the elastomeric domain. Elastin is a key protein component of the extracellular matrix (ECM). EBPs have been modified to have thermal sensitivity based on the elastomeric domain, and have the pentapeptide Val-Pro-(Gly or Ala)-Xaa-Gly [VP(G or A)XG] (SEQ ID NO 26), which consists of five amino acids, as repeat units. EBPs are thermally sensitive polypeptides, and they form drug delivery nanostructures as their transition temperatures are controlled easily.

The Xaa, which is a guest residue, may be any amino acid other than proline. EBPs may be classified into two kinds depending on the sequence of the repeat unit: one is an elastin-based polypeptide with elasticity (EBPE) having a sequence of Val-Pro-Gly-Xaa-Gly (SEQ ID NO 26, where the A or G is G); and the other is an elastin-based polypeptide with plasticity (EBPP) having a sequence of Val-Pro-Ala-Xaa-Gly (SEQ ID NO 26, where the A or G is A).

EBPs have been designed to have stimuli responsiveness, biocompatibility, biodegradability and nonimmunogenicity on the basis of the elastomeric domain. EBPs are heat-responsive biopolymers consisting of many 'pentapeptide repeat units', Val-Pro-(Gly or Ala)-Xaa-Gly (SEQ ID NO 26), wherein the fourth amino acid Xaa in the repeat unit may be any amino acid other than proline. EBPs have lower critical solution temperature (LCST) behaviors and thus show reversible phase transition depending on temperatures. Their LCST behaviors are advantageous in that inverse transition cycling (ITC) based on protein purification utilizing the thermally induced phase transition of EBPs is possible. The easy purification and stimulation-induced phase transition of EBPs allow genetic fusion of other functional proteins and peptides. For example, EBPs have been used as protein purification tags to increase the production of target proteins such as chloramphenicol acetyltransferase (CAT) or thioredoxin (Trx) without removal of affinity chromatography or protein hydrolysis tags via genetic fusion with the self-cleaving protein intein. Soluble EBPs may be used as 'inert protein-based biomaterials', like poly(ethylene glycol) (PEG), and as 'drug delivery carriers' with drugs or other functional proteins for advanced drug delivery systems, regenerative medicine and tissue engineering.

Recently, a considerable number of cancer-related diseases have been known to result from abnormal angiogenesis in tumors. Physiological angiogenesis in organisms is strictly regulated and is activated only under specific conditions. One of the strategies for controlling angiogenesis is to bind vascular endothelial growth factor (VEGF) to two types of VEGF receptors (VEGFRs), VEGFR1 (fms-like tyrosine kinase-1 or Flt1) and VEGFR2 (kinase insert domain-containing receptor or Flk-1/KDR), present on cell membranes and deliver a growth signal to vascular endothelial cells. Abnormal formation of blood vessels caused by disrupted regulation cause not only cancers but also non-neoplastic diseases. Therefore, various strategies for anti-angiogenesis have been employed to inhibit angiogenesis in tumor growth, cancer cell metastasis, retinal neovascularization, choroidal neovascularization and various diseases such as diabetic retinopathy and asthma. Examples include initiating an anti-angiogenic signal using angiogenesis inhibitors such as caffeic acid (CA) and pigment epithelium-derived factor (PEDF), and blocking angiogenesis signals by interfering with the binding of VEGF to receptors thereof (VEGFRs). Although the specific functions of the VEGFRs have not been completely understood, it was identified through gene deletion studies that VEGFR1 and VEGFR2 induce angiogenesis via different effects. In mice lacking VEGF and VEGFR1 genes, blood vessels were not formed due to overgrowth of endothelial cells, and the endothelial cells and hematopoietic cells did not develop normally. In order to inhibit angiogenesis without damage of endothelial cells and hematopoietic cells, a strategy of interfering with the binding of VEGF and VEGFR1 using biomacromolecules or peptides having high affinity for VEGFR1 has been developed. The anti-Flt1 peptide identified by PS-SPCL (positional scanning-synthetic peptide combinatorial library) screening, which is one of high-throughput screening (HTS) systems, is a hexapeptide having an amino acid sequence of Gly-Asn-Gln-Trp-Phe-Ile (GNQWFI) (SEQ ID NO 3). The anti-Flt1 peptide binds specifically to VEGFR1 as a VEGFR1-specific antagonist, thereby preventing VEGFR1 from interacting with all VEGFR1 ligands including placental growth factor (PlGF) and VEGF/PlGF heterodimer, as well as VEGF. To increase the half-life of the anti-Flt1 peptide in vivo, anti-Flt1 peptide-hyaluronate (HA) conjugates have been studied in connection with the formation of self-assembled micelle structures which encapsulate genistein, dexamethasone or tyrosine-specific protein kinase inhibitors. Although conjugation of the anti-Flt1 peptide with HA polymers increases the half-life of the anti-Flt1 peptide in the body, conjugation efficiency and micelle structures are heterogeneous due to the inconsistency of the molecular weight of polydisperse HA polymers, random distribution and conjugation efficiency of HA and the anti-Flt1 peptide.

Another strategy for inhibiting angiogenesis is to activate anti-angiogenic signals. Pigment epithelium-derived factor (PEDF) not only activates anti-angiogenic signals but also maintains balanced angiogenesis as an angiogenesis inhibitor, and has neurotrophic and antitumorigenic properties. Two peptides derived from PEDF, PEDF 44-mer peptide (residues 58-101) and PEDF 34-mer peptide (residues 24-57), have been identified together with their functions and mechanisms. The PEDF 44-mer peptide blocks vascular leakage and has neurotrophic function. In tumor cells, the PEDF 44-mer peptide induces neuroendocrine differentiation and neurite outgrowth. The PEDF 34-mer peptide inhibits angiogenesis and tumor cells through various pathways. The PEDF 34-mer peptide activates JNK (c-jun-NH2 kinases) and inactivates NFAT (nuclear factor of activated T cells). The activated JNK interferes with the expression of endogenous caspase inhibitor and c-FLIP (cellular FLICE (FADD-like IL-1β-converting enzyme)-inhibitory protein) and restores the inactivated state of NFAT for apoptosis. The inactivated NFAT interferes with basic fibroblast growth factor (bFGF)- and vascular endothelial growth factor (VEGF)-induced transcription for inhibition of angiogenesis. The PEDF 34-mer peptide has binding affinity for the catalytic β-subunit of F1-ATP synthase, which is for inhibiting the activity of ATP synthase. ATP deficiency on cell surface limits tumor growth and invasion. The PEDF 34-mer peptide has binding affinity for the laminin receptor of the endothelial cell membrane. Laminin is a major component of the basal lamina which is one of the basement membranes of endothelial cells. The PEDF 34-mer peptide bound to the laminin receptor induces apoptosis and inhibits tube formation of endothelial cells.

The inventors of the present disclosure have researched to introduce stimuli-responsive elastin-based polypeptides (EBPs) into nanostructures in the form of helix-based cages, and have completed the present disclosure.

DISCLOSURE OF THE INVENTION

Technical Goals

The present disclosure is directed to providing a new fusion polypeptide for inhibiting angiogenesis.

The present disclosure is also directed to providing a composition for treating a disease caused by angiogenesis, which contains the fusion polypeptide for inhibiting angiogenesis.

The present disclosure is also directed to providing a fusion protein nanocage having a peptide for inhibiting angiogenesis.

The present disclosure is also directed to providing a theranostic nanoprobe for a disease caused by angiogenesis.

Technical Solutions

The present disclosure provides a fusion polypeptide for inhibiting angiogenesis,
  i) consisting of an anti-angiogenic peptide; a helix-based polypeptide represented by SEQ ID NO 1, which is linked to the peptide; a hydrophilic elastin-based polypeptide (hydrophilic EBP) linked to the helix-based peptide; and a helix-based polypeptide represented by SEQ ID NO 2, which is linked to the hydrophilic EBP,
  ii) consisting of a helix-based polypeptide represented by SEQ ID NO 1; a first hydrophilic EBP linked to the peptide; an anti-angiogenic peptide linked to the first hydrophilic EBP; a second hydrophilic EBP linked to the anti-angiogenic peptide; and a helix-based polypeptide represented by SEQ ID NO 2, which is linked to the second hydrophilic EBP, or
  iii) consisting of an anti-angiogenic peptide; a helix-based polypeptide represented by SEQ ID NO 1, which is linked to the peptide; a hydrophilic EBP linked to the helix-based polypeptide; an anti-angiogenic peptide linked to the hydrophilic EBP; a hydrophilic EBP linked to the anti-angiogenic peptide; and a helix-based polypeptide represented by SEQ ID NO 2, which is linked to the hydrophilic EBP.

The anti-angiogenic peptide may be an anti-Flt1 peptide [SEQ ID NO 3] or a PEDF (pigment epithelial-derived factor) 34-mer [SEQ ID NO 4], although not being necessarily limited thereto.

The PEDF 34-mer is a fragment of PEDF consisting of 34 amino acids and is known in the art to have anti-angiogenic property.

The anti-Flt1 peptide inhibits formation of new blood vessels by binding specifically to Flt1, which is a vascular endothelial growth factor (VEGF) receptor. The PEDF (pigment epithelial-derived factor) is a peptide which inhibits angiogenesis.

The hydrophilic EBP may be represented by one of SEQ ID NOS 5 to 14. But, it may be any hydrophilic EBP that can be used in the art without being necessarily limited thereto.

The i) may consist of [anti-Flt1 peptide of SEQ ID NO 3]-[helix-based polypeptide represented by SEQ ID NO 1]-[hydrophilic EBP]-[helix-based polypeptide represented by SEQ ID NO 2].

The ii) may consist of [helix-based polypeptide represented by SEQ ID NO 1]-[hydrophilic EBP]-[EDF 34-mer of SEQ ID NO 4]-[hydrophilic EBP]-[helix-based polypeptide represented by SEQ ID NO 2].

The iii) may consist of [anti-Flt1 peptide of SEQ ID NO 3]-[helix-based polypeptide represented by SEQ ID NO 1]-[hydrophilic EBP]-[EDF 34-mer of SEQ ID NO 4]-[hydrophilic EBP]-[helix-based polypeptide represented by SEQ ID NO 2].

The i) may be represented by SEQ ID NO 16, the ii) may be represented by SEQ ID NO 17, and the iii) may be represented by SEQ ID NO 18.

In another aspect, the present disclosure provides a composition for treating a disease caused by angiogenesis, which contains the fusion polypeptide for inhibiting angiogenesis mentioned above.

The disease caused by angiogenesis may be one or more selected from a group consisting of diabetic retinopathy, retinopathy of prematurity, macular degeneration, choroidal neovascularization, neovascular glaucoma, ocular disease caused by corneal neovascularization, corneal transplantation rejection, corneal edema, corneal opacity, cancer, hemangioma, angiofibroma, rheumatoid arthritis and psoriasis, although not being necessarily limited thereto.

In another aspect, the present disclosure provides a fusion protein nanocage having a peptide for inhibiting angiogenesis, which is prepared as the helix-based polypeptide represented by SEQ ID NO 1 and the helix-based polypeptide represented by SEQ ID NO 2 in the fusion polypeptide for inhibiting angiogenesis mentioned above self-assemble.

The nanocage may have a multivalent fusion polypeptide for inhibiting angiogenesis.

In an exemplary embodiment of the present disclosure, the fusion polypeptide has an anti-Flt1 peptide and a PEDF 34-mer at the same time.

In another aspect, the present disclosure provides a theranostic nanoprobe for a disease caused by angiogenesis, which includes:
  a fluorescent dye; and
  the fusion protein nanocage having a peptide for inhibiting angiogenesis mentioned above,
  wherein the fluorescent dye is held in the nanocage.

In another aspect, the present disclosure provides a theranostic nanoprobe for a disease caused by angiogenesis, which includes:
  a Raman dye-bound metal nanoparticle; and
  the fusion protein nanocage having a peptide for inhibiting angiogenesis mentioned above,
  wherein the fluorescent dye is held in the nanocage.

The disease caused by angiogenesis may be one or more selected from a group consisting of diabetic retinopathy, retinopathy of prematurity, macular degeneration, choroidal neovascularization, neovascular glaucoma, ocular disease caused by corneal neovascularization, corneal transplantation rejection, corneal edema, corneal opacity, cancer, hemangioma, angiofibroma, rheumatoid arthritis and psoriasis, although not being necessarily limited thereto.

The term "anti-angiogenic peptide" used in the present disclosure refers to a peptide which inhibits formation of new blood vessels. As a specific example, the anti-Flt1 peptide inhibits formation of new blood vessels by specifically binding to Flt1, which is a vascular endothelial growth factor (VEGF) receptor. The PEDF (pigment epithelial-derived factor) 34-mer is a peptide which inhibits angiogenesis.

The fusion polypeptide of the present disclosure inhibits the formation of new blood vessels.

The term "amino acid" used in the present disclosure refers to a natural amino acid or an artificial amino acid. Specifically, it refers to a natural amino acid. For example, the amino acid refers to glycine, alanine, serine, valine, leucine, isoleucine, methionine, glutamine, asparagine, cysteine, histidine, phenylalanine, arginine, tyrosine, tryptophan, etc.

The properties of these amino acids are widely known in the art. Specifically, they exhibit hydrophilicity (negatively or positively charged) or hydrophobicity, and have aliphatic or aromatic properties.

The abbreviations used in the present specification such as Gly (G), Ala (A), etc. are abbreviations of amino acids. Gly is an abbreviation of glycine, and Ala is an abbreviation of alanine. Glycine is also represented by G, and alanine is also represented by A. These abbreviations are widely used in the art.

In the present disclosure, "hydrophilic amino acids" refer to amino acid exhibiting hydrophilic properties and include lysine, arginine, etc.

The term "polypeptide" used in the present disclosure refers to any polymer chain of amino acids. The terms "peptide" and "protein" may be used interchangeably with the term polypeptide and also refer to a polymer chain of amino acids. The term "polypeptide" includes natural or synthetic proteins, protein fragments and polypeptide analogues of protein sequences. The polypeptide may be a monomer or a polymer.

In the present disclosure, the "elastin-based polypeptide (EBP)" is also called an "elastin-like polypeptide (ELP)". It is a term widely used in the technical field of the present disclosure.

In the present specification, the Xaa (or X) is called a "guest residue". Various kinds of EBPs according to the present disclosure can be prepared by introducing various Xaa's.

The EBPs undergo reversible phase transition at a lower critical solution temperature (LCST), also called a transition temperature ($T_t$). They are highly water-soluble below the $T_t$, but become insoluble at temperatures higher than the $T_t$.

In the present disclosure, the physical and chemical properties of EBPs are controlled mainly be a combination of Val-Pro-(Gly or Ala)-Xaa-Gly, which is a pentapeptide repeat unit. Specifically, the third amino acid of the repeat unit determines relative mechanical property. For example, in the present disclosure, the third amino acid Gly determines elasticity and Ala determines plasticity. The elasticity or plasticity appears after transition.

Meanwhile, the hydrophobicity of the fourth amino acid, i.e., the guest residue Xaa, and the multimerization of the pentapeptide repeat unit affect the $T_t$.

The EBP according to the present disclosure may be a polypeptide wherein the pentapeptide is repeated, and the repeating polypeptides may form a polypeptide block (EBP block). Specifically, a hydrophilic EBP block or a hydrophobic EBP block may be formed. The hydrophilic or hydrophobic of the EBP block of the present disclosure is closely related with the transition temperature of the EBP.

The transition temperature of the EBP also depends on amino acid sequence and molecular weight. The relationship between the sequence of the EBP and the $T_t$ was studied a lot by Urry et al. (Urry D. W., Luan C.-H., Parker T. M., Gowda D. C., Parasad K. U., Reid M. C., and Safavy A. 1991. Temperature of polypeptide inverse temperature transition depends on mean residue hydrophobicity. J. Am. Chem. Soc. 113: 4346-4348). Urry et al. found out that, when the fourth amino acid, i.e., the "guest residue" Val, in the pentapeptide of Val-Pro-Gly-Val-Gly (SEQ ID NO 24) is replaced with a more hydrophilic residue, $T_t$ is increased as compared to the original sequence. In contrast, when Val was replaced with a more hydrophobic guest residue, $T_t$ was decreased as compared to the original sequence. That is to say, it was found out that hydrophilic EBPs have higher $T_t$ and hydrophobic EBPs have relatively lower $T_t$. Through this finding, it has become possible to prepare an EBP having a specific $T_t$ by determining which amino acid to use as a guest residue of the EBP sequence and varying the composition of the guest residue (Protein-Protein Interactions: A Molecular Cloning Manual, 2002, Cold Spring Harbor Laboratory Press, Chapter 18. pp. 329-343).

As described above, hydrophilicity, high $T_t$ leads to hydrophilicity and low $T_t$ leads to hydrophobicity. The $T_t$ of the EBP blocks according to the present disclosure can also be increased or decreased by changing the amino acid sequence and molecular weight including of the guest residue. As a result, hydrophilic EBP blocks or hydrophobic EBP blocks can be prepared.

For reference, an EBP having a $T_t$ lower than body temperature may be used as a hydrophobic block, and an EBP having a $T_t$ higher than body temperature may be used as a hydrophilic block. Due to these characteristics of EBPs, the hydrophilic and hydrophobic properties of EBPs can be defined relatively in bioengineering applications.

Taking the EBP sequence of the present disclosure as an example, when a plastic polypeptide block in which a plastic pentapeptide Val-Pro-Ala-Xaa-Gly (SEQ ID NO 26, where the G or A is A) is repeated is compared with an elastic polypeptide block which an elastic pentapeptide Val-Pro-Gly-Xaa-Gly (SEQ ID NO 26, where the G or A is A) is repeated, the third amino acid Gly exhibits higher hydrophilicity than Ala. Accordingly, the plastic polypeptide block (elastin-based polypeptide with plasticity: EBPP) exhibits a lower $T_t$ than the elastic polypeptide block (elastin-based polypeptide with elasticity: EBPE).

As described above, the EBPs according to the present disclosure may be made to exhibit hydrophilic or hydrophobic properties by adjusting $T_t$.

In the present disclosure, the "helix-based polypeptide" refers to a helical polypeptide, specifically one derived from ferritin.

Ferritin is an intercellular protein which stores and releases iron. Ferritin self-assembles to form a protein cage. The cage protein is a protein capable of forming a macromolecule with a molecular weight of tens to hundreds of times that of small-molecular-weight monomers through elaborate self-assembly. Ferritin exists generally in the form of a hollow spherical cage in vivo, wherein the cage is composed of helical bundles (ferritin A, B, C and D) and a short fifth helix (ferritin E).

The helix-based polypeptide of the present disclosure is also denoted as "HPC (helix-based protein cage)", and is expressed by SEQ ID NO 1 representing the helical bundles (ferritin A, B, C and D; denoted as 'HPC4' in examples) and SEQ ID NO 2 representing the short fifth helix (ferritin E; denoted as 'HPC5' in examples).

In the present disclosure, the "theranostic nanoprobe" refers to a nano-sized probe allowing therapy and diagnosis at the same time.

The "nano" includes a range of size understood by those of ordinary skill in the art. The range of size may be specifically from 0.1 to 1000 nm, more specifically from 10 to 1000 nm, further more specifically from 20 to 500 nm, even more specifically from 40 to 250 nm.

In the present disclosure, the "Raman dye" refers to an organic compound used in a measurement method based on surface-enhanced Raman scattering (SERS). A Raman signal is measured based on SERS using a metal nanoparticle to which the Raman dye is attached. This technology is widely known in the art.

The "Raman dye" may be any one widely known in the art without limitation. Specific examples may include rhodamine 6G, rhodamine B isothiocyanate (RBITC), adenine, 4-amino-pyrazolo(3,4-d)pyrimidine, 2-fluoroadenine, N6-benzoyladenine, kinetin, dimethylallylaminoadenine, zeatin, bromoadenine, 8-azaadenine, 8-azaguanine, 6-mercaptopurine, 4-amino-6-mercaptopyrazolo(3,4-d)pyrimidine, 8-mercaptoadenine, 9-aminoacridine, etc., although not being necessarily limited thereto.

In the present disclosure, the "multivalent fusion protein nanocage having a peptide for inhibiting angiogenesis" refers to a nanocage structure including a fusion polypeptide including one or more peptide for inhibiting angiogenesis. Specifically, it refers to a nanostructure including a fusion polypeptide which includes both a peptide binding specifically to vascular endothelial growth factor (VEGF) receptor (Flt1 or Flk-1/KDR) and pigment epithelium-derived factor (PEDF) which is an angiogenesis inhibitor.

In the present disclosure, the "fusion protein nanocage" is also expressed as a "fusion protein cage".

The fusion polypeptide according to the present disclosure is schematically shown in FIG. 1.

In the present disclosure, a specific class of stimuli-responsive elastin-based polypeptides (EBPs) have been introduced into a ferritin nanostructure for non-chromatographic purification and exposure of a therapeutic domain.

As a specific example, [anti-Flt1 peptide of SEQ ID NO 3] was linked to the N-terminal of [helix-based polypeptide represented by SEQ ID NO 1], and [hydrophilic EBP]-[EDF 34-mer of SEQ ID NO 4]-[hydrophilic EBP]-[helix-based polypeptide represented by SEQ ID NO 2] was linked sequentially to the other terminal of [helix-based polypeptide represented by SEQ ID NO 1].

In the present disclosure, a fusion protein cage having a multivalent peptide for inhibiting angiogenesis has been developed by a genetic engineering technology for treatment of uncontrolled angiogenesis-dependent diseases. The fusion polypeptide consists of a helix-based protein cage (HPC) for self-assembly, a heat-sensitive EBP and two anti-angiogenic peptides (anti-Flt1 peptide and PEDF 34-mer peptide). The HPC is derived from ferritin consisting of four helical bundles (SEQ ID NO 1) and a relatively short helix (SEQ ID NO 2). The two different anti-angiogenic peptides are located at the exposed parts of HPC and EBP, respectively. They have been introduced for effective exposure of the PEDF 34-mer peptide and non-chromatographic purification. Two EBP monoblocks have been fused between the PEDF 34-mer peptide for effective exposure of the PEDF 34-mer peptide. The EBP-PEDF 34-mer-EBP triblock copolypeptide is located between the fourth and fifth helices of HPC. The anti-Flt1 peptide is located at the N-terminal of HPC, which is another exposed part. The fusion polypeptide self-assembles into a nanocage structure having multivalent anti-angiogenic effect. The inventors of the present disclosure have developed a fusion protein cage utilizing the VEGFR binding affinity of the anti-Flt1 peptide and the iron storage and pH responsiveness characteristics of HPC.

Cell imaging and sensing functions have been added to the fusion protein by conjugating a fluorescent (Raman) dye to HPC for surface-enhanced Raman scattering (SERS)-based sensing and synthesizing gold nanoparticles (AuNPs) inside the HPC. The fluorescent dye-conjugated fusion protein cage has been shown to bind to VEGFR (vascular endothelial growth factor receptor) in cell membrane, exhibit angiogenesis-inhibiting effect and allowing cell imaging.

The fusion protein cage has been developed as a SERS-based sensing probe by reducing gold ions accumulated in HPC to AuNPs and introducing a Raman dye onto the surface of the AuNPs. The Raman dye is introduced to the AuNP surface by passing through the fusion protein cage when it is in unfolded under an acidic condition. The cage structure is restored under a neutral condition. The self-assembly and aggregation of the fusion protein cage with time have been identified by dynamic light scattering (DLS). The anti-angiogenesis and cell imaging characteristics of the fusion protein have been studied in vitro using human umbilical vein endothelial cells (HUVECs).

A therapeutic composition containing the fusion polypeptide for inhibiting angiogenesis of the present disclosure is a pharmaceutical composition. The pharmaceutical composition contains the fusion polypeptide and may contain other substances that do not interfere with use for anti-angiogenic purposes in vivo. The other substances may include a diluent, an excipient, a carrier and/or another substance for inhibiting angiogenesis, without limitation.

In some exemplary embodiments, the fusion polypeptide for inhibiting angiogenesis of the present disclosure is prepared for normal administration to the human body, for example, together with a suitable diluent including sterile water and ordinary saline.

The therapeutic composition according to the present disclosure may be administered or delivered via any route that can access a target tissue. For example, the administration may be made by direct injection into the target tissue (e.g., cardiac tissue) such as topical, intradermal, subcutaneous, intramuscular, intraperitoneal, intraarterial, intracoronary, intradural intravenous or intravitreal injection. The fusion polypeptide disclosed in the present disclosure can be administered via a convenient route including subcutaneous, intradermal, intravenous and intramuscular routes in consideration of stability and/or efficacy.

The present disclosure provides a method for delivering the fusion polypeptide (e.g., as contained in a composition or a preparation described in the present disclosure) and a method for treating, alleviating or preventing the progress of a disease in a subject. The term "subject" or "patient" used in the present disclosure refers to any vertebrate including, but not limited to, human and other primates (e.g., chimpanzee, other apes and monkeys), farm animals (e.g., cow, sheep, pig, goat and horse), pets (e.g., dog and cat), laboratory animals (e.g., rodents such as mouse, rat and guinea pig) and birds (e.g., poultry such as chicken and turkey, wild or game birds, duck, goose, etc.). In some exemplary embodiments, the subject is a mammal.

In another exemplary embodiment, the mammal is human.

The fusion polypeptide or pharmaceutical composition of the present disclosure may be contacted with a target cell (e.g., mammalian cell) in vitro or in vivo.

In another aspect, the present disclosure provides a method for treating or preventing a disease caused by angiogenesis, which includes a step of administering the therapeutic composition according to the present disclosure to a subject.

For clinical use, the fusion polypeptide of the present disclosure may be administered alone via any suitable administration route effective to achieve a desired therapeutic result or may be formulated into a pharmaceutical composition. The administration "route" of the fusion polypeptide of the present disclosure may include enteral, parenteral and topical administration or inhalation. The enteral administration route of the fusion polypeptide of the present disclosure includes oral, gastrointestinal, intestinal and rectal routes. The parenteral route includes intraocular, intravenous, intraperitoneal, intramuscular, intraspinal, subcutaneous, topical, vaginal, nasal, mucosal and pulmonary administration. The topical administration route of the fusion polypeptide of the present disclosure refers to external application of the fusion polypeptide into the epidermis, mouth, ears, eyes or nose.

The therapeutic composition may be administered by parenteral administration, oral administration, transdermal administration, sustained release, controlled release, delayed release, suppository administration, catheter administration or sublingual administration.

When the fusion polypeptide in the therapeutic composition is administered together with another drug, it may be administered at an amount of 15 mg/kg or less for intravenous injection and 2.5 mg or less for intravitreal injection.

The present disclosure is described further by the following additional examples that should not be construed as limiting. Those of ordinary skill will appreciate in light of the present disclosure that many changes can be made to the specific exemplary embodiments which are disclosed herein and still obtain a similar or comparable result without departing from the spirit and scope of the present disclosure.

Unless defined otherwise, all the technical and scientific terms used in the present specification have the same meaning as commonly understood by those of ordinary skill in the art to which the present disclosure belongs. In general, the nomenclatures used in the present specification are well known and commonly used in the art.

Effects

A self-assembled fusion protein cage having anti-angiogenic and angiogenic cell-imaging functions of the present disclosure provides a new way for advanced drug delivery systems for treating angiogenesis-related diseases such as retinal neovascularization, corneal neovascularization, choroidal neovascularization, tumor growth, cancer cell metastasis, diabetic retinopathy and asthma.

MODE FOR CARRYING OUT THE INVENTION

Example 1: Materials

Figure 1:
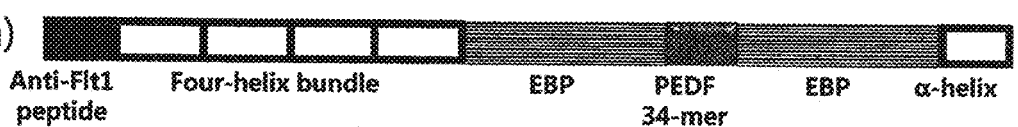
FIG. 1 (A) shows amino acid sequences of an anti-Flt1 peptide (SEQ ID NO 3), a PEDF 34-mer (SEQ ID NO 4) and EBPP[$A_1G_4I_1$]$_1$ (SEQ ID NO 6), and (B) and (C) show designing and application of an anti-Flt1-HPC-EBPP [$A_1G_4I_1$]$_{12}$-PEDF 34-mer fusion polypeptide block. (B) (a) The anti-Flt1 peptide is located at the N-terminal and the EBPP[$A_1G_4I_1$]$_6$-PEDF 34-mer-EBPP[$A_1G_4I_1$]$_6$ triblock is located between the fourth and fifth helices of HPC. (b) The self-assembled structure of the fusion polypeptide has been modified for bioimaging and biosensing. A fluorescent dye has been labeled in a cage for bioimaging, and a gold nanoparticle was synthesized in the cage structure and conjugated with the Raman dye for biosensing. (C) The anti-angiogenic function of a fusion protein cage has been induced by two mechanisms. The anti-Flt1 peptide inhibits intracellular angiogenic signals, and the PEDF 34-mer activates anti-angiogenic signals.
Figure 1:
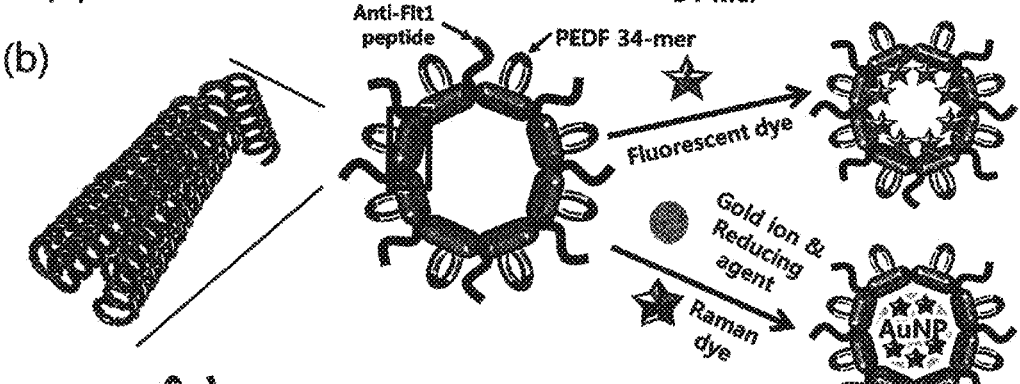
Figure 1:
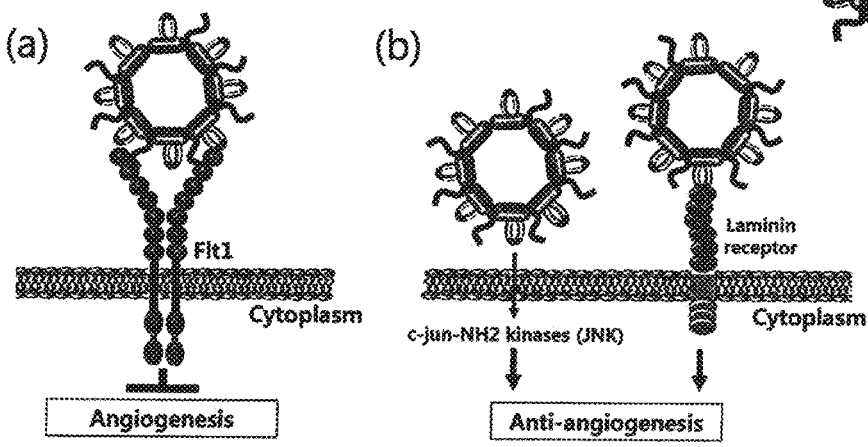

A pET-21a (+) vector and BL21 (DE3)E. coli cells were obtained from Novagen Inc. (Madison, WI, U.S.). Top10 competent cells and calcein-AM were purchased from Invitrogen (Carlsbad, CA, U.S.), and HUVECs were purchased from Lonza (Basel, Switzerland). All customized oligonucleotides were synthesized by Cosmo Gene Tech (Seoul, South Korea) and human recombinant VEGF-165 (rhVEGF$_{165}$) was obtained from R&D Systems (Minneapolis, U.S.). CIP (calf intestinal alkaline phosphatase), BamHI and XbaI were purchased from Thermo Fisher Scientific (Waltham, MA, U.S.). AcuI and BseRI were purchased from New England Biolabs (Ipswich, MA, U.S.). T4 DNA ligase was purchased from Elpis Bio-tech (Taejeon, South Korea).

DNA miniprep, gel extraction and PCR purification kits were purchased from Geneall Biotechnology (Seoul, South Korea). Dyne Agarose High was purchased from DYNE BIO, Inc. (Seongnam, South Korea). The Top10 cells were grown in TB DRY media obtained from MO BIO Laboratories, Inc. (Carlsbad. CA, U.S.). The BL21 (DE3) cells were grown in Circle Grow media purchased from MP Biomedicals (Solon, OH, U.S.). The HUVECs cells were grown with EGM-2 Bullet Kit and EBM-2 purchased from Lonza (Basel, Switzerland). Ready Gels (Tris-HCl 2-20% precast gels) were purchased from Bio-Rad (Hercules, CA, U.S.). PBS (phosphate-buffered saline, pH 7.4) and ampicillin were purchased from Sigma-Aldrich (St Louis, MO, U.S.). Matrigel was purchased from BD Biosciences (San Diego, CA, U.S.). Human recombinant $VEGF_{165}$ protein and human recombinant VEGF R1/Flt-1 $F_c$ were purchased from R&D System (Minneapolis, MN, U.S.). Gold(III) chloride trihydrate, sodium borohydride, ascorbic acid and malachite green isothiocyanate were purchased from Sigma-Aldrich (St Louis, MO, U.S.).

Example 2: Notation for Different EBP Blocks and Block Polypeptides Thereof

Different EBPs having a pentapeptide repeat unit Val-Pro-(Gly or Ala)-$X_{aa}$-Gly [VP(G or A)XG] (SEQ ID NO 26) are named as follows. The $X_{aa}$ may be any amino acid other than Pro. First, a pentapeptide repeat of Val-Pro-Ala-$X_{aa}$-Gly (VPAXG) (SEQ ID NO 26, where the G or A is A) having plasticity is defined as an elastin-based polypeptide with plasticity (EBPP). On the other hand, a pentapeptide repeat of Val-Pro-Gly-$X_{aa}$-Gly (VPGXG) (SEQ ID NO 26, where the G or A is G) is called an elastin-based polypeptide with elasticity (EBPE). Second, in $[X_iY_jZ_k]_n$, the capital letters in the parenthesis represent the single-letter amino acid codes of guest residues, i.e., the amino acids at the fourth position ($X_{aa}$ or X) of the EBP pentapeptide, and subscripts corresponding to the capital letters indicate the ratio of the guest residues in an EBP monomer gene as repeat units. The subscript number n in $[X_iY_jZ_k]_n$ (i+j+k=6) represents the total number of repeats of EBP of the present disclosure, i.e., [VPGXG VPGXG VPGXG VPGXG VPGXG VPGXG] (SEQ ID NO 27) or [VPAXG VPAXG VPAXG VPAXG VPAXG VPAXG] (SEQ ID NO 28). For example, EBPP $[A_1G_4I_1]_6$ is an EBPP block consisting of 6 repeats of [VPAXG VPAXG VPAXG VPAXG VPAXG VPAXG] (SEQ ID NO 28), in which the ratio of Ala, Gly and Ile at the fourth guest residue position ($X_{aa}$) is 1:4:1. Finally, a diblock polypeptide of EBPP with another peptide is named according to the composition of each block in brackets with a hyphen between the blocks, e.g., as $EBPP[A_1G_4I_1]_6$-HPC5.

Example 3: Preparation of Modified pET-21a Vector for Seamless Gene Cloning

A pET-21a vector was treated with XbaI, BamHI and CIP at 37° C. for 20 minutes in FastDigest buffer and then dephosphorylated. The restriction enzyme-treated plasmid DNA was purified using a PCR purification kit and then eluted with deionized water. Two oligonucleotides with XbaI- and BamHI-compatible sticky ends were designed as follows.

```
                                              (SEQ ID NO 19)
5'-ctagaaataattttgtttaactttaagaaggaggagtacatatggg
ctactgataatgatcttcag-3'.

(SEQ ID NO 20)
5'-gatcctgaagatcattatcagtagcccatatgtactcctccttctt
aaagttaaacaaaattattt-3'.
```

The two oligonucleotides were annealed in T4 DNA ligase buffer by heating at 95° C. for 2 minutes and then cooled slowly to room temperature over 3 hours. The annealed double-stranded DNA (dsDNA), i.e., a DNA insert, was ligated into the multiple cloning site (MCS) of the linearized pET-21a vector by treating with T4 DNA ligase in T4 DNA ligase buffer and incubating at 37° C. for 30 minutes. For seamless cloning and expression, the gene recombinant pET-21a (mpET-21a) vector was transformed into Top10 competent cells, which were then plated on an SOC (super optimal broth with catabolite repression) plate treated with 50 μg/mL ampicillin. The DNA base sequence of the mpET-21a vector was verified by fluorescent dye terminator DNA sequencing (Applied Biosystems Automatic DNA Sequencer ABI 3730).

Example 4: Synthesis of EBP Monomers and Oligomerization Thereof

The base sequences of EBPPs including a 'pentapeptide repeat unit' Val-Pro-Ala-$X_{aa}$-Gly (SEQ ID NO 26, where the A or G is A), in which the ratio of Ala, Gly and Ile at the fourth residue is 1:4:1, were designed to optimize $T_t$ below a physiological temperature. A pair of oligonucleotides for encoding $EBPP[A_1G_4I_1]_1$ were annealed in T4 DNA ligase buffer by heating at 95° C. for 3 minutes and then cooled slowly to room temperature over 3 hours. The mpET-21a cloning vector was treated with BseRI and CIP at 37° C. for 30 minutes and then dephosphorylated. The restriction enzyme-treated plasmid DNA was purified using a PCR purification kit and then eluted with deionized water. The annealed dsDNA and the linearized mpET-21a cloning vector were treated with T4 DNA ligase in T4 DNA ligase buffer and then ligated by incubating at 16° C. for 30 minutes. The ligated plasmid was transformed into Top10 chemically competent cells and then plated onto an SOC plate treated with 50 μg/mL ampicillin. DNA base sequence was then confirmed by DNA sequencing. A gene was prepared until the repeat number was 6, i.e., $EBPP[A_1G_4I_1]_6$.

EBP sequences having a pentapeptide repeat unit Val-Pro-(Gly or Ala)-$X_{aa}$-Gly (SEQ ID NO 26) in which the fourth residue were varied with different molar ratios were designed at DNA level to optimize $T_t$ below a physiological temperature. The amino acid sequences of EBPs having various pentapeptide repeat units are shown in Table 1.

TABLE 1

Amino acid sequences of EBP

| EBP | Amino acid sequence | SEQ ID NO |
|---|---|---|
| EBPE[$A_1G_4I_1$] | VPGGG VPGAG VPGGG VPGGG VPGIG VPGGG | 5 |
| EBPP[$A_1G_4I_1$] | VPAGG VPAAG VPAGG VPAGG VPAIG VPAGG | 6 |
| EBPE[$K_1G_4I_1$] | VPGGG VPGKG VPGGG VPGGG VPGIG VPGGG | 7 |
| EBPP[$K_1G_4I_1$] | VPAGG VPAKG VPAGG VPAGG VPAIG VPAGG | 8 |
| EBPE[$D_1G_4I_1$] | VPGGG VPGDG VPGGG VPGGG VPGIG VPGGG | 9 |
| EBPP[$D_1G_4I_1$] | VPAGG VPADG VPAGG VPAGG VPAIG VPAGG | 10 |
| EBPE[$E_1G_4I_1$] | VPGGG VPGEG VPGGG VPGGG VPGIG VPGGG | 11 |
| EBPP[$E_1G_4I_1$] | VPAGG VPAEG VPAGG VPAGG VPAIG VPAGG | 12 |

PEDF cDNA fragment 34-mer (130-23) was amplified from human PEDF cDNA fragments by PCR by using the following primers.

```
(forward)
                                      (SEQ ID NO 21)
5'-AAAGGATCCCCCTACTGGTAATGCTCTTCAGTCTAGAGAT-3'

(reverse)
                                      (SEQ ID NO 22)
5'-CACGACCAACGGCTACTGATAGTGATCTTCAGCTAGCGAT-3'
```

The forward primer had an XbaI restriction enzyme site at 3'-end, and the reverse primer had a NheI restriction enzyme site at 5'-end. The two primers had AcuI restriction enzyme and recognition sites for seamless cloning of a gene including EBPP[$A_1G_4I_1$]$_n$. An insert gene was constructed by treating the amplified gene fragments of PEDF 34-mer with XbaI and NheI in CutSmart buffer at 37° C. for 2 hours. After the treatment, the product was electrophoresed on agarose gel and the insert gene was purified using a gel extraction kit. The pET-21a cloning vector was treated with XbaI and CIP at 37° C. for 1 hour and then dephosphorylated. The restriction enzyme-treated DNA was purified using a PCR purification kit and eluted with deionized water. The restriction enzyme-treated PEDF 34-mer gene fragment and the linearized pET-21a cloning vector were ligated by treating with T4 DNA ligase in T4 DNA ligase buffer and incubating at 16° C. for 30 minutes. The ligation product was transformed into Top10 chemically competent cells, which were then plated on an SOC plate treated with 50 μg/mL ampicillin. The transformant was initially screened by diagnostic restriction enzyme treatment on agarose gel and further confirmed by DNA sequencing as described above.

Example 6: Construction of HPC (Helix-Based Protein Cage)-Encoding Gene in Cloning Vector For fusion with genes of other peptides between helical bundles (ferritin A, B, C and D) and a short fifth helix (ferritin E), genes encoding the four helical bundles and a gene encoding the fifth helix were cloned into mPET-21a. The genes encoding the four helical bundles, having XbaI and BamHI restriction enzyme sites at both ends, were delivered to the pUCIDT vector. An insert gene was constructed by treating the plasmid including the four helical bundles with 10 U of XbaI and 10 U of BamHI in CutSmart buffer at 37° C. for 2 hours. After the treatment, the product was electrophoresed on agarose gel and the insert gene was purified using a gel extraction kit. A total of 4 μg of the mpET-21a cloning vector was treated with restriction enzymes and then dephosphorylated with 15 U of XbaI, 10 U of BamHI and 10 U of FastAP thermosensitive alkaline phosphatase at 37° C. for 1 hour. The plasmid DNA was purified using a PCR purification kit and eluted with 40 μL of distilled, deionized water. After treating 90 pmol of the gene fragments of the four helical bundles and 30 pmol of the linearized mpET-21a cloning vector with 1 U of T4 DNA ligase in T4 DNA buffer, ligation was performed by incubating at 16° C. for 30 minutes. The ligated product was transformed into Top10 competent cells and then plated onto an SOC plate treated with 50 μg/mL ampicillin. The transformant was initially screened by diagnostic restriction enzyme treatment on agarose gel and further confirmed by DNA sequencing as described above. A 57-bp gene encoding the fifth helix, having sticky ends of GG-5' and 3'-CC was constructed through hybridization. A pair of oligonucleotides (50 μL, 2 μM) encoding the fifth helix were heated at 95° C. for 3 minutes in T4 DNA ligase buffer and then slowly cooled to room temperature over 3 hours. A total of 4 μg of the mpET-21a cloning vector was treated with restriction enzymes and then dephosphorylated by treating with 15 U of BseRI and 10 U of FastAP as a thermosensitive alkaline phosphatase at 37° C. for 30 minutes. The plasmid DNA was purified using a PCR purification kit and eluted with 40 μL of distilled, deionized water. After treating 90 pmol of annealed double-stranded DNA (dsDNA) and 30 pmol of the linearized mpET-21a cloning vector with 1 U of T4 DNA ligase in T4 DNA buffer, ligation was performed by incubating at 16° C. for 30 minutes. The ligated product was transformed into Top10 chemically competent cells and then plated onto an SOC plate treated with 50 μg/mL ampicillin. DNA sequence was confirmed by DNA sequencing.

Example 7: Construction of Gene of Anti-Flt1-HPC4-EBP-PEDF 34-Mer-HPC5 Fusion Protein Cage A pair of oligonucleotides encoding an anti-Flt1 peptide acting as a VEGFR1 antagonist were synthesized chemically by Cosmo Genetech (Seoul, Korea) and linked to an oligonucleotide cassette with sites recognized by AcuI and BseRI. For seamless cloning, the oligonucleotide cassette encoding the anti-Flt1 peptide was designed rationally to have no BseRI, XbaI, AcuI and BamHI restriction sites. Each plasmid containing EBPP[A₁G₄I₁]₆ having BseRI, XbaI, AcuI and BamHI restriction sites, PEDF 34-mer, the fragments of four helical bundles of HPC and the fragment of the fifth helix of HPC and the oligonucleotide cassette were used to create genes for a fusion polypeptide library of anti-Flt1-four helical bundles (HPC4)-EBPP[A₁G₄I₁]₆-PEDF 34-mer-EBPP[A₁G₄I₁]₆-fifth helix (HPC5). For encoding of the fusion polypeptide library, a plasmid vector encoding the fifth helix was treated with 15 U of BseRI in CutSmart buffer at 37° C. for 1 hour. The restriction enzyme-treated plasmid DNA was purified using a PCR purification kit and then dephosphorylated by treating with 10 U of FastAP as a thermosensitive alkaline phosphatase in CutSmart buffer at 37° C. for 1 hour. The restriction enzyme-treated and dephosphorylated plasmid DNA was purified using a PCR purification kit and then eluted with 40 μL of distilled, deionized water. For construction of an insert gene, 4 mg of the EBPP[A₁G₄I₁]₆ gene was treated with 10 U of BseRI and 15 U of AcuI in CutSmart buffer at 37° C. for 1 hour. After the treatment, the product was electrophoresed on agarose gel and the insert gene was purified using a gel extraction kit. 90 pmol of the purified insert gene and 30 pmol of the linearized vector were ligated by treating with 1 U of T4 DNA ligase in T4 DNA ligase buffer and incubating at 16° C. for 30 minutes. The ligated product was transformed into Top10 chemically competent cells, which were then plated onto an SOC plate treated with 50 μg/mL ampicillin. The transformant was initially screened by diagnostic restriction enzyme treatment on agarose gel and further confirmed by DNA sequencing. A plasmid vector including the insert DNA was constructed by the method described above. For construction of the insert gene, PEDF 34-mer was prepared by PCR and restriction enzyme treatment and the oligonucleotide cassette encoding the anti-Flt1 peptide was used as the insert gene. The insert gene of the four helical bundles was prepared by the same method as the EBPP[A₁G₄I₁]₆ insert gene. Ligation was performed as described above.

the polypeptide was induced by adding IPTG to a final concentration of 1 mM. The cells were centrifuged at 4500 rpm for 10 minutes at 4° C. The expressed EBPs and block polypeptides thereof were purified by ITC as described above. The cell pellet including the EBPs was resuspended in 30 mL of PBS buffer and the EBPs were purified with PBS. The cell pellet including the fusion protein cage was resuspended in 30 mL of PBS containing 3 M urea and then purified with PBS containing 3 M urea to denature the helical structure of NPC. The cells were lysed by sonication (VC-505, Sonic and materials Inc., Danbury, CT) on ice bath for 10 seconds with 20-second intervals. The cell lysate was centrifuged in a 50-mL centrifuge tube at 13000 rpm for 15 minutes at 4° C. to precipitate insoluble debris. The supernatant containing soluble EBPs was transferred to a new 50-mL centrifuge tube and centrifuged with 0.5% w/v PEI at 13000 rpm for 15 minutes at 4° C. to precipitate nucleic acid contaminants. The inverse phase transition of the EBPs was triggered by adding NaCl at a final concentration of 3 M, and the aggregated EBPs were separated from the lysate solution by centrifuging at 13000 rpm for 15 minutes at 4° C. The aggregated EBPs were resuspended in cold buffer and centrifuged at 13000 rpm for 15 minutes at 4° C. to remove aggregated protein contaminants. These aggregation and resuspension processes were repeated 5-10 times until the EBP purity reached about 95% when determined by SDS-PAGE.

FIG. 1 shows the amino acid sequences of the anti-Flt1 peptide, PEDF 34-mer and EBPP$[A_1G_4I_1]_1$, a strategy for designing of the blocks of the EBPP$[A_1G_4I_1]_{12}$-PEDF 34-mer fusion polypeptide, self-assembly of the fusion polypeptide, modification of the self-assembled structure for bioimaging and biosensing, and anti-angiogenic function of the self-assembled fusion protein cage via two mechanisms. The amino acid sequences of HPC (SEQ ID NOS 1 and 2), anti-Flt1 peptide (SEQ ID NO 3), PEDF 34-mer peptide (SEQ ID NO 4) and EBPP$[A_1G_4I_1]$ (SEQ ID NO 6) are shown in Table 2 and FIG. 1 (A).

TABLE 2

| | | |
|---|---|---|
| SEQ ID NO 1 | HPC4 | SSQIRQNYSTDVEAAVNSLVNLYLQASYTYLSLGF YFDRDDVALEGVSHFFRELAEEKREGYERLLKMQ NQRGGRALFQDIKKPAEDEWGKTPDAMKAAMAL EKKLNQALLDLHALGSARTDPHLCDFLETHFLDEE VKLIKKMGDHLTNLHRLGG |
| SEQ ID NO 2 | HPC 5 | PEAGLGEYLFERLTLKHD |
| SEQ ID NO 3 | Anti-FM peptide | GNQWFI |
| SEQ ID NO 4 | PEDF 34-mer | DPFFKVPVNKLAAAVSNFGYDLYRVRSSTSPTTN |
| SEQ ID NO 6 | EBPP$[A_1G_4I_1]_1$ | VPAGG VPAAG VPAGG VPAGG VPAIG VPAGG |

Example 8: Expression and Purification of EBP and Fusion Protein Cage Genes

*E. coli* strain BL21 (DE3) cells were transformed with each vector containing EBP and fusion protein cages, and then inoculated in 50 mL of CircleGrow medium supplemented with 50 μg/mL ampicillin. Preculture was performed in a shaking incubator at 200 rpm overnight at 37° C. Then, after inoculating 50 mL of TB DRY medium with 500 mL of CircleGrow medium supplemented with 50 μg/mL ampicillin, the cells were cultured in a shaking incubator at 200 rpm for 16 hours at 37° C. When absorbance (optical density) at 600 nm ($OD_{600}$) reached 1.0, overexpression of FIG. 1 (B) shows (a) a strategy for designing of the blocks of the anti-Flt1-HPC-EBPP$[A_1G_4I_1]_{12}$-PEDF 34-mer fusion polypeptide and (b) a self-assembled structure, modification of the structure by conjugation of a fluorescent dye and a strategy for synthesis of the Raman dye conjugated on gold nanoparticles (AuNPs) for bioimaging and biosensing. HPC consists of four helical bundles (hereinafter, denoted as 'HPC4') and a relatively short helix (α-helix, hereinafter, denoted as 'HPC5'). It self-assembles into a nanocage, and there are exposed parts at the N-terminal and between the fourth and fifth helices. Two anti-angiogenic peptides (anti-Flt1 peptide and PEDF 34-mer peptide) were fused at the exposed parts of HPC. The anti-Flt1 peptide was located at the N-terminal of HPC, and the EBPP[$A_1G_4I_1$]$_6$-PEDF 34-mer-EBPP[$A_1G_4I_1$]$_6$ was located between the fourth and fifth helices. The EBP block was introduced to effectively expose the PEDF 34-mer peptide and purify the fusion polypeptide by a non-chromatographic method. The fusion protein cage was conjugated with the fluorescent dye at cysteine via a thiol-maleimide reaction. For surface-enhanced Raman scattering (SERS)-based application, AuNPs were synthesized inside the HPC structure by accumulation and reduction of gold ions. The AuNP-containing structure was partially broken to introduce the Raman dye onto the AuNP surface and then was restored to its original structure. For anti-angiogenic function, the fusion polypeptide was composed of the anti-Flt1 peptide and the PEDF 34-mer having different mechanisms (FIG. 1 (C)). The anti-Flt1 peptide inhibited intracellular angiogenic signaling and interfered with the interaction between VEGF and VEGFR1 by binding to VEGFR1 (Flt1). The PEDF 34-mer, which is the region of anti-angiogenesis function of PEDF, induced intracellular anti-angiogenic signaling. In order to study the anti-angiogenic function of the fusion protein cage depending on the anti-Flt1 peptide and PEDF 34-mer, four types of fusion polypeptides, i.e., a fusion polypeptide with neither the anti-Flt1 peptide nor the PEDF 34-mer, a fusion polypeptide including the anti-Flt1 peptide or the PEDF 34-mer and a fusion polypeptide including the anti-Flt1 peptide and the PEDF 34-mer, were designed.

Example 9: Characterization of EBPs and Anti-Flt1-HPC4-EBP-PEDF 34-Mer-HPC5 Fusion Protein Cage The purity of EBPs and the fusion protein cage was determined by SDS-PAGE. The effect of temperature on the inverse phase transition of the EBPs and fusion protein cage at 25 μM in PBS was investigated by measuring $OD_{350}$ using the Cary 100 Bio UV/Vis spectrophotometer equipped with a multi-cell thermoelectric temperature controller (Varian Instruments, Walnut Creek, CA) from 10 to 85° C. at a heating rate of 1° C./min. The self-assembly and thermal sensitivity of the fusion protein cage were identified using a temperature-controlled Nano ZS90 (ZEN3690) dynamic light scattering (DLS) instrument (Malvern instruments, Worcestershire, UK). Their hydrodynamic radius ($R_H$) at 25 μM in PBS was measured in 11 successive runs at each temperature in a temperature range from 20 to 60° C. at a heating rate of 1° C./min. Their $T_t$ was defined as the onset temperature of phase transition and was calculated from each DLS plot.

Example 10: In Vitro Tube Formation Assay of HUVECs Using Fusion Protein Cage

In vitro tube formation assay of HUVECs was performed using the fusion protein cages to evaluate their effects on the proliferation, migration and tube formation of the endothelial cells. For Matrigel coating, 200 μL of Matrigel was solidified on a 48-well plate by incubating at 37° C. for 30 minutes. For fluorescence labeling, HUVECs were incubated with 0.5 μM calcein-AM at 37° C. for 15 minutes. In order to investigate how the proliferation, migration and tube formation of the endothelial cells are affected, the calcein-labeled HUVECs were spread on the Matrigel-coated well plate at $4\times10^4$ cells/well and were incubated with 50 ng/mL human recombinant rhVEGF$_{165}$ and fusion protein cage at 37° C. for 4 hours. The tube formation of the HUVECs was imaged with a micromanipulator (Zeiss, Oberkochen, Germany) and quantified by measuring whole tube length in three random fields per well with an angiogenesis analyzer of the Image J lab software. The tube formation was repeated three times.

Example 11: HUVEC Imaging Using Fluorescent Dye-Conjugated Fusion Protein Cage

For in-vitro cell imaging, the fusion protein cage was labeled with Alexa Fluor 488 C5 maleimide. 50 μM of the fusion protein cage was incubated with 500 μM of Alexa Fluor C5 maleimide at room temperature for 2 hours in 0.01 M PBS containing 3 M urea and 10 mM DTT. The remaining Alexa Fluor 488 C5 maleimide was removed by dialyzing with PBS. The label was characterized with a fluorescence spectrum (Ex: 480; Em: 500-550, Ex slit 10 nm; Em slit 5 nm) in SDS-PAGE without staining with a fluorescent protein. HUVECs were spread onto a 48-well plate at $4\times10^4$ cells/well and then cultured overnight. The HUVECs were incubated with 50 ng/mL human recombinant rhVEGF$_{165}$ and dye-conjugated fusion protein cage at different concentrations for 15, 30 and 60 minutes at 37° C. The HUVECs were imaged in a bright-field mode with a micromanipulator (Zeiss, Oberkochen, Germany) using FITC.

Example 12: Synthesis of Gold Nanoparticles Inside Cage Structure of Fusion Protein Cage and Conjugation of Raman Dye to Gold Nanoparticles After incubating 25 μM fusion protein cage with 0.2 mM HAuCl$_4$ at room temperature for 3 hours in 0.01 M PBS, unbound HAuCl$_4$ was removed from the surface by washing twice with PBS. Then, gold ions were removed by adding 1 mM NaBH$_4$ to the gold seeds. The resulting solution was pale yellow. After water quenching for 3 hours, incubation was performed for 1 hour after further adding 0.2 mM HAuCl$_4$. Then, 1 mM ascorbic acid was added so that the gold seeds grew into gold nanoparticles (AuNPs). The final solution was ruby red. The nanoparticles synthesized in the protein cage were characterized by measurement of absorbance at 350 to 900 nm and TEM imaging.

Due to conjugation of a Raman dye to the gold nanoparticles (AuNPs) in the protein cage structure, the pH of 0.01 M PBS buffer containing AuNP-protein was decreased to pH 6.0, lower than the pI of the fusion protein (6.029), as HCl was added. 10 μM MGITC was added to the 0.01M PBS buffer of pH 6.0. The pH of the buffer was increased to pH 7.4 at 1 hour after the addition of NaOH. Raman measurement was performed by Raman spectroscopy (Renishaw 2000, Renishaw, UK).

Results

Figure 2:
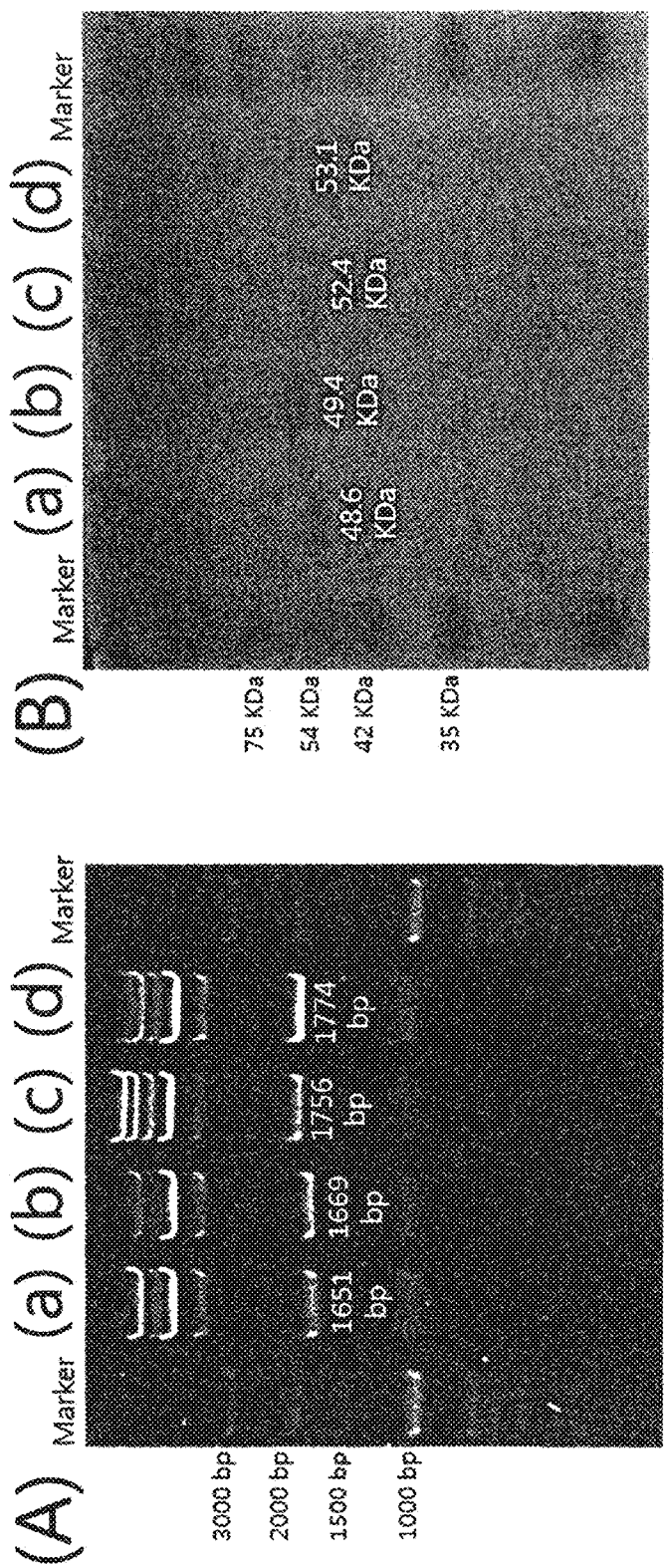
FIG. 2 shows (A) agarose gel (1%) and (B) SDS-PAGE gel images of (a) HPC4-EBPP[$A_1G_4I_1$]$_{12}$-HPC5, (b) anti-Flt1-HPC4-EBPP[$A_1G_4I_1$]$_{12}$-HPC5, (c) HPC4-EBPP [$A_1G_4I_1$]$_6$-PEDF 34-mer-EBPP[$A_1G_4I_1$]$_6$-HPC5 and (d) anti-Flt1-HPC4-EBPP[$A_1G_4I_1$]$_6$-PEDF 34-mer-EBPP [$A_1G_4I_1$]$_6$-HPC5. (A) A modified pET21-a(+) plasmid encoding the fusion protein has been treated with Xba I and AcuI restriction enzymes. The length of gene fragments including the fusion protein cage is indicated below the gene fragments. (B) The fusion protein cage has been expressed in E. coli and purified by ITC. The gel was visualized by copper staining. The predicted molecular weight is indicated below bands.

A fusion protein cage consisting of anti-Flt1-peptide, PEDF 34-mer and EBP was constructed by cloning of a gene encoding the fusion protein cage and IPTG-induced overexpression of the fusion protein cage. The gene encoding the fusion protein cage was constructed by inserting genes encoding EBPP[$A_1G_4I_1$]$_6$, PEDF 34-mer, four helices of HPC and anti-Flt1 peptide sequentially into a plasmid including the fifth helix of HPC. The insertion of each gene was confirmed by treatment with XbaI and AcuI restriction enzymes, agarose gel electrophoresis and DNA sequencing. The constructed four genes encoding the fusion protein cage, (a) HPC4-EBPP[$A_1G_4I_1$]$_{12}$-HPC5, (b) anti-Flt1-HPC4-EBPP[$A_1G_4I_1$]$_{12}$-HPC5, (c) HPC4-EBPP[$A_1G_4I_1$]$_6$-PEDF 34-mer-EBPP[$A_1G_4I_1$]$_6$-HPC5 and (d) anti-Flt1-HPC4-EBPP[$A_1G_4I_1$]$_6$-PEDF 34-mer-EBPP[$A_1G_4I_1$]$_6$-HPC5, are shown in FIG. 2 (A). The gene encoding the fusion protein cage was treated with XbaI and AcuI, and the length of the DNA fragments of each gene is shown. The DNA length of the genes encoding (a) HPC4-EBPP[$A_1G_4I_1$]$_{12}$-HPC5-HPC5, (b) anti-Flt1-HPC4-EBPP[$A_1G_4I_1$]$_{12}$-HPC5, (c) HPC4-EBPP[$A_1G_4I_1$]$_6$-PEDF 34-mer-EBPP[$A_1G_4I_1$]$_6$-HPC5 and (d) anti-Flt1-HPC4-EBPP[$A_1G_4I_1$]$_6$-PEDF 34-mer-EBPP[$A_1G_4I_1$]$_6$-HPC5 was 1614, 1632, 1719 and 1737 bp, respectively. Because the XbaI restriction enzyme site was present in the gene of the fusion protein cage, the length of the DNA fragments was larger than the original gene length as 37 bp.

The fusion protein cage was expressed in *E. coli* and purified by inverse transition cycling (ITC). The purity and molecular weight of the purified fusion protein cage were identified by copper-stained SDS-PAGE in order to visualize protein bands (FIG. 2(B)). The expected molecular weights of (a) HPC4-EBPP[$A_1G_4I_1$]$_{12}$-HPC5, (b) anti-Flt1-HPC4-EBPP[$A_1G_4I_1$]$_{12}$-HPC5, (c) HPC4-EBPP[$A_1G_4I_1$]$_6$-PEDF 34-mer-EBPP[$A_1G_4I_1$]$_6$-HPC5 and (d) anti-Flt1-HPC4-EBPP[$A_1G_4I_1$]$_6$-PEDF 34-mer-EBPP[$A_1G_4I_1$]$_6$-HPC5 are indicated below each band (48.6, 49.4, 52.4, and 53.1 kDa, from left to right), and the rightmost lane on the SDS-PAGE gel represents the shift of a standard protein size marker. The shift of the fusion protein cage did not match with the shift of the standard protein size marker. The four fusion protein cages shifted more than theoretical molecular weights, and anti-Flt1-HPC4-EBPP[$A_1G_4I_1$]$_{12}$-HPC5 showed a larger molecular weight than HPC4-EBPP[$A_1G_4I_1$]$_6$-PEDF 34-mer-EBPP[$A_1G_4I_1$]$_6$-HPC5. It was previously reported that EBP shifted about 20% more than theoretical molecular weight in SDS-PAGE (McPherson, D. T.; Xu, J.; Urry, D. W. *Protein Expression Purif,* 1996, 7 (1), 51-7; Meyer, D. E.; Chilkoti, A. *Biomacromolecules* 2002, 3 (2), 357-367; McDaniel, J. R.; MacKay, J. A.; Quiroz, F. G.; Chilkoti, A. *Biomacromolecules* 2010, 11 (4), 944-952). Anti-Flt1-HPC4-EBPP[$A_1G_4I_1$]$_{12}$-HPC5 showed a larger molecular weight than HPC4-EBPP[$A_1G_4I_1$]$_6$-PEDF 34-mer-EBPP[$A_1G_4I_1$]$_6$-HPC5 because it had a longer EBP block than HPC4-EBPP[$A_1G_4I_1$]$_6$-PEDF 34-mer-EBPP[$A_1G_4I_1$]$_6$-HPC5 having two EBPP[$A_1G_4I_1$]$_6$ blocks.

Figure 3:
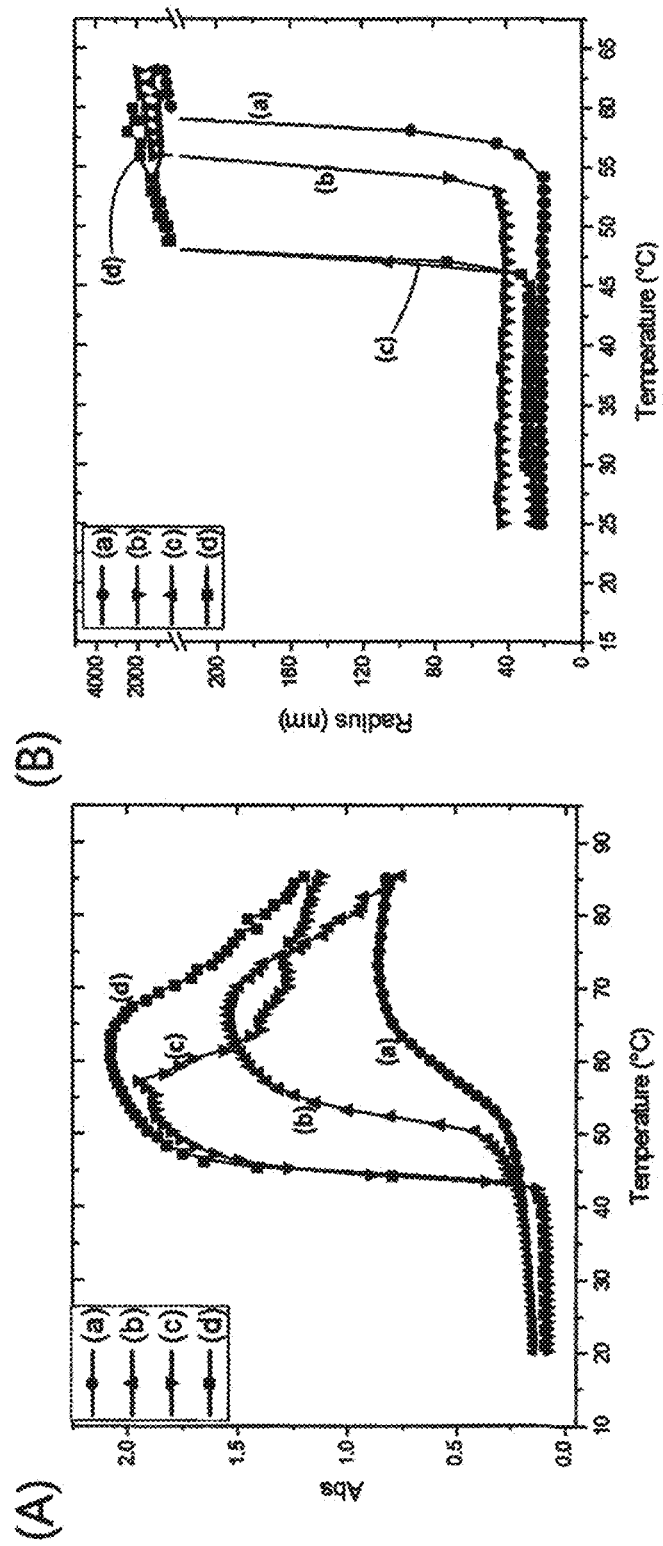
FIG. 3 shows (A) turbidity profiles and (B) hydrodynamic radii of (a) HPC4-EBPP[$A_1G_4I_1$]$_{12}$-HPC5, (b) anti-Flt1-HPC4-EBPP[$A_1G_4I_1$]$_{12}$-HPC5, (c) HPC4-EBPP[$A_1G_4I_1$]$_6$-PEDF 34-mer-EBPP[$A_1G_4I_1$]$_6$-HPC5 and (d) anti-Flt1-HPC4-EBPP[$A_1G_4I_1$]$_6$-PEDF 34-mer-EBPP[$A_1G_4I_1$]$_6$-HPC5 at 25 µM in 0.01 M PBS. The absorbance at 350 nm and hydrodynamic radius were measured while heating at a rate of 1° C./min.

The thermal sensitivity of the fusion protein cage was determined by measuring the absorbance of the polypeptide solution depending on increase in temperature in order to monitor phase transition. Turbidity profiles were obtained by measuring the absorbance of 25 µM fusion protein cage in 10 mM PBS at 350 nm while heating at a rate of 1° C./min (FIG. 3 (A)). Phase transition temperature ($T_t$) was defined as the inflection point of each thermal plot in FIG. 3 (A) and summarized in Table 3.

The turbidity at $T_t$ is due to the self-assembled cage structure of the fusion protein cage. The absorbance was increased at temperatures above $T_t$. The $T_t$ of HPC4-EBPP[$A_1G_4I_1$]$_{12}$-HPC5, anti-Flt1-HPC4-EBPP[$A_1G_4I_1$]$_{12}$-HPC5, HPC4-EBPP[$A_1G_4I_1$]$_6$-PEDF 34-mer-EBPP[$A_1G_4I_1$]$_6$-HPC5 and anti-Flt1-HPC4-EBPP[$A_1G_4I_1$]$_6$-PEDF 34-mer-EBPP[$A_1G_4I_1$]$_6$-HPC5 was 55.12, 52.24, 44.17 and 44.37° C., respectively. The $T_t$ of anti-Flt1-HPC4-EBPP[$A_1G_4I_1$]$_{12}$-HPC5 was decreased by 2.85° C. as compared to that of HPC4-EBPP[$A_1G_4I_1$]$_{12}$-HPC5. However, there was no significant difference in $T_t$ among HPC4-EBPP[$A_1G_4I_1$]$_6$-PEDF 34-mer-EBPP[$A_1G_4I_1$]$_6$-HPC5 and anti-Flt1-HPC4-EBPP[$A_1G_4I_1$]$_6$-PEDF 34-mer-EBPP[$A_1G_4I_1$]$_6$-HPC5. The fusion protein cage including PEDF 34-mer had a lower $T_t$ than the fusion protein cage not including PEDF 34-mer. The $T_t$ of HPC4-EBPP[$A_1G_4I_1$]$_6$-PEDF 34-mer-EBPP[$A_1G_4I_1$]$_6$-HPC5 and anti-Flt1-HPC4-EBPP[$A_1G_4I_1$]$_6$-PEDF 34-mer-EBPP[$A_1G_4I_1$]$_6$-HPC5 was lower than the $T_t$ of HPC4-EBPP[$A_1G_4I_1$]$_{12}$-HPC5 and anti-Flt1-HPC4-EBPP[$A_1G_4I_1$]$_{12}$-HPC5 by 10.85° C. and 7.90° C., respectively. HPC4-EBPP[$A_1G_4I_1$]$_6$-PEDF 34-mer-EBPP[$A_1G_4I_1$]$_6$-HPC5 and anti-Flt1-HPC4-EBPP[$A_1G_4I_1$]$_6$-PEDF 34-mer-EBPP[$A_1G_4I_1$]$_6$-HPC5 had the triblock EBPP[$A_1G_4I_1$]$_6$-PEDF 34-mer-EBPP[$A_1G_4I_1$]$_6$, and anti-Flt1-HPC4-EBPP[$A_1G_4I_1$]$_{12}$-HPC5 had the monoblock EBPP[$A_1G_4I_1$]$_{12}$. Although the EBP length of the fusion protein cage was the same, the number of EBP blocks was 2 times for the triblock EBPP[$A_1G_4I_1$]$_6$-PEDF 34-mer-EBPP[$A_1G_4I_1$]$_6$ than that of the monoblock EBPP[$A_1G_4I_1$]$_{12}$. The $T_t$ of the fusion polypeptide was decreased as the EBP block was split and the PEDF 34-mer was inserted.

The HPC based on the fusion protein cage self-assembled into a cage structure at temperatures lower than $T_t$ and was aggregated at temperatures higher than $T_t$. Their self-assembly and aggregation were characterized by dynamic light scattering (DLS). The hydrodynamic radius ($R_H$) of 25 µM fusion protein cage in 10 mM PBS in a temperature range from 25 to 60° C. was measured 11 successive runs at each temperature while heating at a rate of 1° C./min. Their $T_t$ was defined as the inflection point of each thermal plot in FIG. 3 (B) and summarized in Table 2. The $R_H$ of HPC4-EBPP[$A_1G_4I_1$]$_{12}$-HPC5, anti-Flt1-HPC4-EBPP[$A_1G_4I_1$]$_{12}$-HPC5, HPC4-EBPP[$A_1G_4I_1$]$_6$-PEDF 34-mer-EBPP[$A_1G_4I_1$]$_6$-HPC5 and anti-Flt1-HPC4-EBPP[$A_1G_4I_1$]$_6$-PEDF 34-mer-EBPP[$A_1G_4I_1$]$_6$-HPC5 at temperatures lower than $T_t$ was 20.97, 26.27, 42.90 and 28.93 nm, respectively. The previously reported radius of the self-assembled cage structure was 12 nm. The $R_H$ of the fusion protein cage was larger than the reported size of the HPC cage structure due to the

TABLE 3

| | Transition temperature (° C.) | |
|---|---|---|
| | Abs | DLS |
| HPC4-EBPP[$A_1G_4I_1$]$_{12}$-HPC5 (SEQ ID NO 15) | 55.12 | 59.00 |
| Anti-Flt1-HPC4-EBPP[$A_1G_4I_1$]$_{12}$-HPC5 (SEQ ID NO 16) | 52.27 | 55.18 |
| HPC4-EBPP[$A_1G_4I_1$]$_6$-PEDF 34-mer-EBPP[$A_1G_4I_1$]$_6$-HPC5 (SEQ ID NO 17) | 44.27 | 43.18 |
| Anti-Flt1-HPC4-EBPP[$A_1G_4I_1$]$_6$-PEDF 34-mer-EBPP[$A_1G_4I_1$]$_6$-HPC5 (SEQ ID NO 18) | 44.37 | 49.00 |

EBP at the exposed part. The size of the soluble unimer EBP was reported to be about 10 nm. The measured $R_H$ of the fusion protein cage structure was larger than 20 nm, which corresponded to the $R_H$ expected for the self-assembled cage structure having soluble EBP (~16 nm). At temperatures higher than $T_t$, the $R_H$ value was increased instantaneously to larger than the value of aggregation, 1000 nm. This is consistent with the fact that the fusion protein cage self-assembled at temperatures lower than $T_t$ and was aggregated at temperatures higher than $T_t$.

Figure 4:
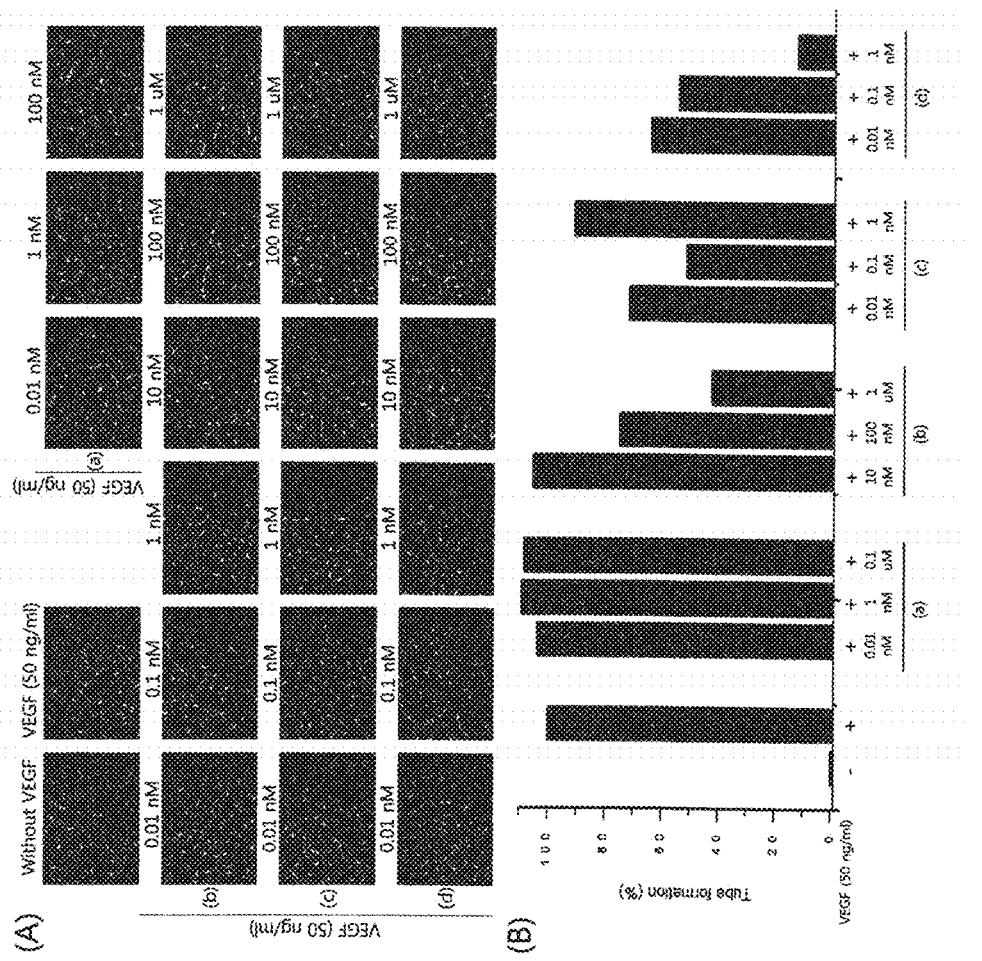
FIG. 4 shows (A) fluorescence microscopic images and (B) degree of tube formation of calcein-AM-labeled HUVECs treated with (a) HPC4-EBPP[$A_1G_4I_1$]$_{12}$-HPC5, (b) anti-Flt1-HPC4-EBPP[$A_1G_4I_1$]$_{12}$-HPC5, (c) HPC4-EBPP[$A_1G_4I_1$]$_6$-PEDF 34-mer-EBPP[$A_1G_4I_1$]$_6$-HPC5 and (d) anti-Flt1-HPC4-EBPP[$A_1G_4I_1$]$_6$-PEDF 34-mer-EBPP [$A_1G_4I_1$]$_6$-HPC5 at 0.01 nM to 10 µM. The formation degree was quantified from the images of (A).

The anti-angiogenic function of the fusion protein cage was investigated in vitro through migration and tube formation assays of HUVECs. For investigation of inhibitory effect on migration and tube formation of HUVECs, calcein-labeled HUVECs were treated for 4 hours with the fusion protein cage at different concentrations on Matrigel to which 50 ng/mL human recombinant VEGF-165 (rhVEGF165) was added. For evaluation of the relationship between the peptides for inhibiting angiogenesis (anti-Flt1 peptide and PEDF 34-mer) and concentrations, HUVECs were incubated with the fusion protein cage including 0.01 nM, 0.1 nM, 1 nM, 10 nM, 0.1 μM, 1 μM or 1 μM HPC4-EBPP$[A_1G_4I_1]_{12}$-HPC5. As a control, HUVECs were treated with HPC4-EBPP$[A_1G_4I_1]_{12}$-HPC5 with no peptide for inhibiting angiogenesis at different concentrations (0.01 nM, 1 nM, 0.1 μM). The inhibition of tube formation of the HUVECs under each condition is shown in FIG. 4 (A), and the quantified inhibitory effect of each fusion protein cage, calculated from the tube length of the HUVECs in the fluorescence images of FIG. 4 (A), is shown in FIG. 4(B). The tube length at each concentration was normalized by setting the tube length of HUVECs in untreated medium at 0% and the tube length of HUVECs treated with rhVEGF165 to induce cellular migration and tube formation at 100%.

The tube length of the HUVECs treated with HPC4-EBPP$[A_1G_4I_1]_{12}$-HPC5 was similar to the tube length of the HUVECs incubated with rhVEGF165, regardless of the concentration of HPC4-EBPP$[A_1G_4I_1]_{12}$-HPC5. This result indicates that HPC4-EBPP$[A_1G_4I_1]_{12}$-HPC5 has no effect on the tube formation of HUVECs. Other three fusion protein cages except the HPC4-EBPP$[A_1G_4I_1]_{12}$-HPC5 showed inhibitory effect at various concentration ranges. The tube formation of the HUVECs incubated with anti-Flt1-HPC4-EBPP$[A_1G_4I_1]_{12}$-HPC5 was decreased as the concentration of anti-Flt1-HPC4-EBPP$[A_1G_4I_1]_{12}$-HPC5 was increased from 100 nM to 1 μM. HPC4-EBPP$[A_1G_4I_1]_6$-PEDF 34-mer-EBPP$[A_1G_4I_1]_6$-HPC5 inhibited the tube formation of HUVECs in the concentration range from 0.01 nM to 0.1 nM, where anti-Flt1-HPC4-EBPP$[A_1G_4I_1]_{12}$-HPC5 had no effect on the tube formation of HUVECs. The HUVECs treated with 1 nM anti-Flt1-HPC4-EBPP$[A_1G_4I_1]_6$-PEDF 34-mer-EBPP$[A_1G_4I_1]_6$-HPC5 showed the least tube formation, and their tube formation was decreased as the concentration of anti-Flt1-HPC4-EBPP$[A_1G_4I_1]_6$-PEDF 34-mer-EBPP$[A_1G_4I_1]_6$-HPC5 was increased from 0.01 nM to 1 nM. Anti-Flt1-HPC4-EBPP$[A_1G_4I_1]_6$-PEDF 34-mer-EBPP$[A_1G_4I_1]_6$-HPC5 effectively inhibited the tube formation of HUVECs at broad concentration ranges of the present disclosure. When the concentration of the fusion protein cage was higher than the effective concentration range, the HUVECs treated with the fusion protein cage including PEDF 34-mer peptide showed a similar degree of tube formation as the HUVECs incubated with rhVEGF165. According to a previous report, the PEDF 34-mer peptide induced the inhibition of angiogenesis by interfering with the expression of endogenous caspase inhibitor and c-FLIP (FLICE-like inhibitory protein) through inactivation of NFAT (nuclear factor of activated T cells) and activation of JNK (c-Jun N-terminal kinase) for inhibition of basic fibroblast growth factor (bFGF) and vascular endothelial growth factor (VEGF). Meanwhile, JNK was reported as a positive regulator of angiogenesis in endothelial cells (ECs). The inhibition of INK attenuated the sprout growth of ECs in 3D capillary sprout culture, reduced the growth and migration of ECs, and decreased the protein level of transcription factor Egr-1, which is a gene regulator involved in cellular growth and migration. This report explains the reason why the fusion protein cage including PEDF 34-mer has no effect at higher concentrations in the tube formation of HUVECs assay.

Figure 5:
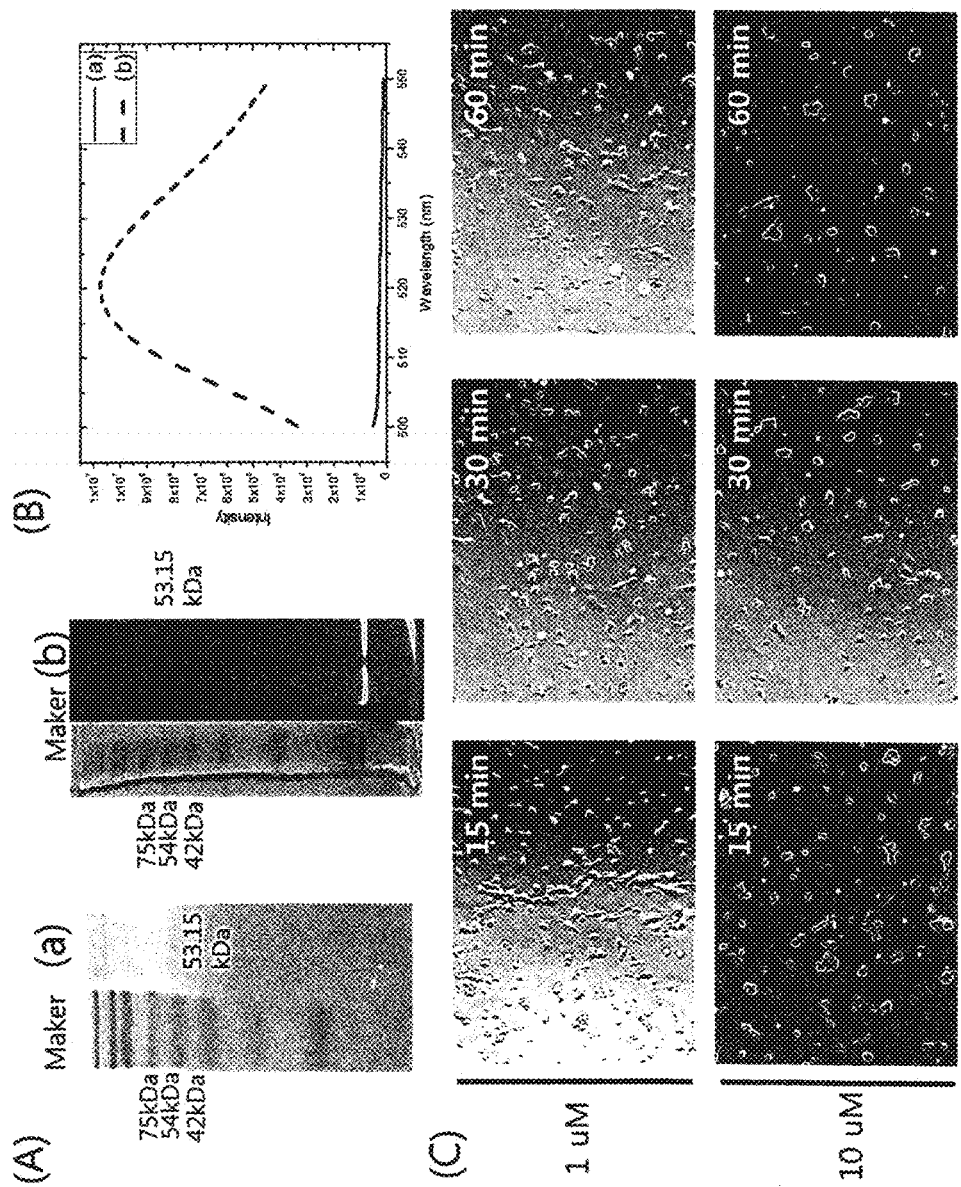
FIG. 5 (A) visualizes a fluorescent dye conjugated with anti-Flt1-HPC4-EBPP[$A_1G_4I_1$]$_6$-PEDF 34-mer-EBPP [$A_1G_4I_1$]$_6$-HPC5 on SDS-PAGE. (a): SDS-PAGE gel stained with copper solution of anti-Flt1-HPC4-EBPP [$A_1G_4I_1$]$_6$-PEDF 34-mer-EBPP[$A_1G_4I_1$]$_6$-HPC5 before fluorescent dye conjugation, (b): gel exposed to UV under fluorescence scanner after fluorescent dye conjugation. (B) shows the fluorescence spectra of (a) anti-Flt1-HPC4-EBPP [$A_1G_4I_1$]$_6$-PEDF 34-mer-EBPP[$A_1G_4I_1$]$_6$-HPC5 and (b) fluorescent dye-conjugated anti-Flt1-HPC4-EBPP[$A_1$ $G_4I_1$]$_6$-PEDF 34-mer-EBPP[$A_1G_4I_1$]$_6$-HPC5. (C) shows the fluorescence images and bright-field merged images of HUVECs treated with 1 or 10 nM dye-conjugated anti-Flt1-HPC4-EBPP[$A_1G_4I_1$]$_6$-PEDF 34-mer-EBPP[$A_1G_4I_1$]$_6$-HPC5 for 15, 30 or 60 minutes. In (C), the scale bar is 200 µm.

The anti-Flt1-HPC4-EBPP$[A_1G_4I_1]_6$-PEDF 34-mer-EBPP$[A_1G_4I_1]_6$-HPC5 that showed the most effective anti-angiogenic function was conjugated with a fluorescent dye as an imaging probe. A maleimide-modified fluorescent dye was conjugated at the thiol of HPC, and the conjugation of the fluorescent dye to the polypeptide was qualitatively identified by SDS-PAGE. The result is shown in FIG. 5 (A). The fluorescent dye-conjugated anti-Flt1-HPC4-EBPP$[A_1G_4I_1]_6$-PEDF 34-mer-EBPP$[A_1G_4I_1]_6$-HPC5 was visualized by exposure to UV light on SDS-PAGE without gel staining. In FIG. 5 (A) (b), the location of the dye-conjugated polypeptide is compared under UV light with that of a marker in a bright-field mode. The location corresponded to that of the fusion polypeptide on the copper-stained SDS-PAGE gel prior to the dye conjugation (FIG. 5 (A) (a)). The conjugation of the dye to anti-Flt1-HPC4-EBPP$[A_1G_4I_1]_6$-PEDF 34-mer-EBPP$[A_1G_4I_1]_6$-HPC5 was confirmed from the fluorescence spectrum. Whereas the fluorescent dye-conjugated fusion protein cage showed a fluorescence spectrum, the fusion protein cage showed no fluorescence signal prior to the conjugation (FIG. 5 (B)). HUVECs were spread onto a 45-well plate and then cultured overnight. The HUVECs were incubated with 1 μM or 10 μM dye-conjugated polypeptide for 15, 30 or 60 minutes. FIG. 5 (C) shows the fluorescence images and bright-field merged images of the HUVECs treated with the dye-conjugated polypeptide. The HUVECs became rounder as the concentration of the dye-conjugated polypeptide and the incubation time were increased, and the round cells exhibited fluorescence signals. The anti-Flt1 of anti-Flt1-HPC4-EBPP$[A_1G_4I_1]_6$-PEDF 34-mer-EBPP$[A_1G_4I_1]_6$-HPC5 peptide binds to VEGFR1 (Flt1) on the membrane of HUVECs, and inhibits intracellular angiogenic signaling by interfering with the binding of VEGF to VEGFR1. One of the intracellular angiogenic signaling induced by VEGFR1 is the PI-3K (phosphatidylinositol 3-kinase) pathway. It regulates the motility of endothelial cells during migration through regulation of actin-regulating protein for protrusion of lamellipodia and extension of cells. In the fluorescence images of HUVECs shown in FIG. 5 (C), the HUVECs treated with high-concentration dye-conjugated polypeptide for a long time interacted more with the anti-Flt1 of anti-Flt1-HPC4-EBPP$[A_1G_4I_1]_6$-PEDF 34-mer-EBPP$[A_1G_4I_1]_6$-HPC5. The HUVECs had a round shape and exhibited fluorescence signals.

Figure 6:
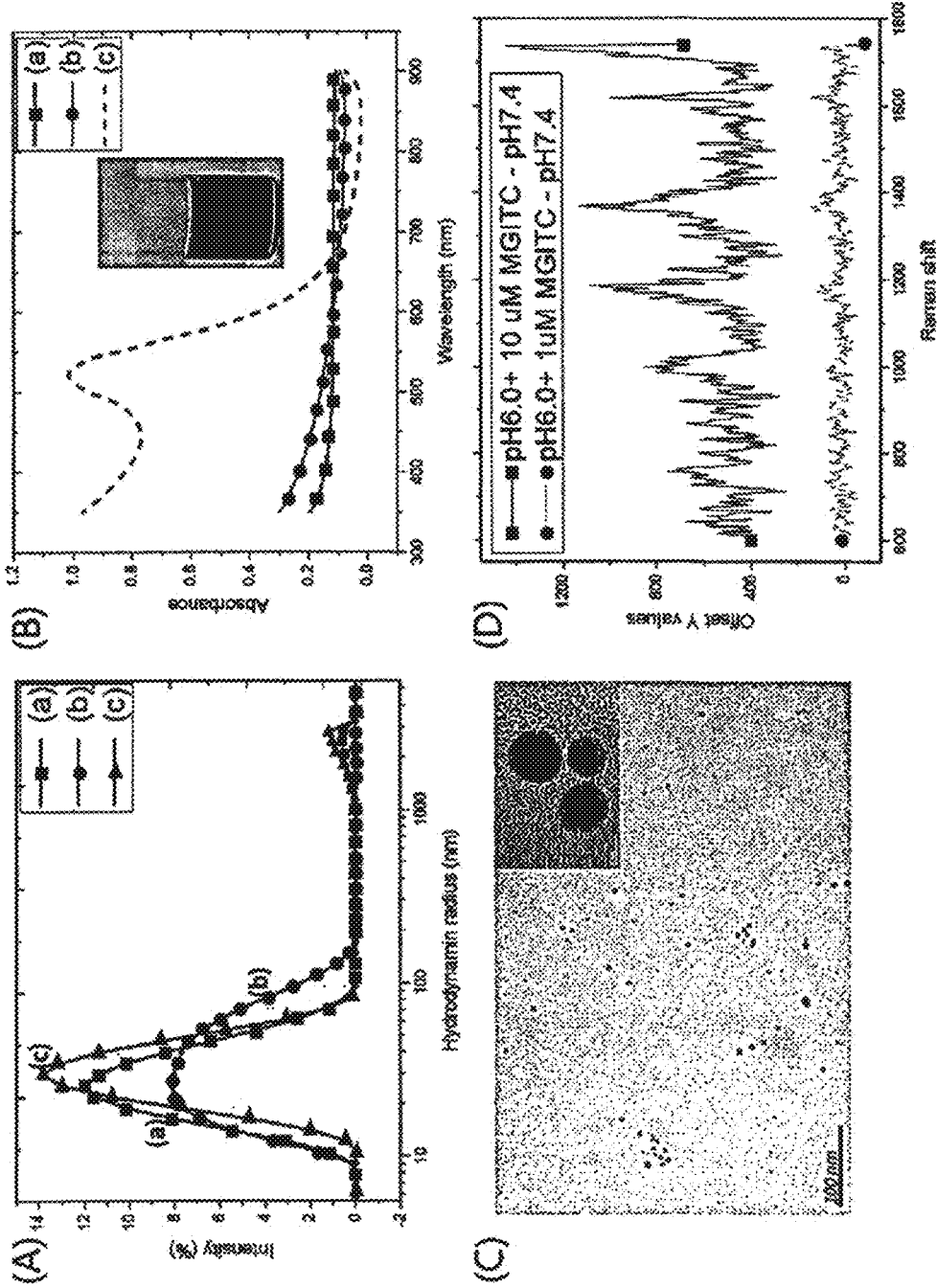
FIG. 6 shows (A) hydrodynamic radius and (B) UV absorption spectra of anti-Flt1-HPC4-EBPP[$A_1G_4I_1$]$_6$-PEDF 34-mer-EBPP[$A_1G_4I_1$]$_6$-HPC5 before treatment with gold ions (a), after synthesis of gold seeds (b) and after growth of gold nanoparticles (c). (C) shows the TEM image of gold nanoparticles inside the fusion protein cage. (D) shows the Raman spectrum of gold nanoparticles conjugated with a Raman dye in the fusion protein cage.

The application of the fusion polypeptide as a cell imaging probe was studied through fluorescence imaging of HUVECs. Another application of the fusion polypeptide is to introduce a Raman dye for Raman sensing by synthesizing gold nanoparticles (AuNPs) inside the cage structure. The HPC of the fusion protein cage has a binding site for inorganic ions including gold ions. The anti-Flt1-HPC4-EBPP$[A_1G_4I_1]_6$-PEDF 34-mer-EBPP$[A_1G_4I_1]_6$-HPC5 which inhibited angiogenesis the most effectively and had a potential for a cell imaging probe was incubated with gold ions for coordination with HPC. The gold ions coordinated with HPC were reduced to gold seeds, and the gold seeds grew into gold nanoparticles by addition of a reducing agent. FIG. 6 (A) shows the size of anti-Flt1-HPC4-EBPP[$A_1G_4I_1$]$_6$-PEDF 34-mer-EBPP[$A_1G_4I_1$]$_6$-HPC5 (a) before incubation with gold ions, (b) after the addition of gold ions and first reduction, and (c) after second reduction. The UV-VIS absorbance in each step is shown in FIG. 6 (B). The coordinated gold ions were reduced and formed seeds inside HPC. The seeds grew until they filled the hollow cavity. As shown in FIG. 6 (A), the size of the fusion protein cage was constant during the synthesis of AuNPs. The synthesis of AuNPs was verified from the absorption spectra. After the second reduction, only anti-Flt1-HPC4-EBPP[$A_1G_4I_1$]$_6$-PEDF 34-mer-EBPP[$A_1G_4I_1$]$_6$-HPC5 showed the absorbance at 520 nm from AuNPs (FIG. 6 (B)). FIG. 6 (C) shows the TEM image of AuNPs inside the anti-Flt1-HPC4-EBPP[$A_1G_4I_1$]$_6$-PEDF 34-mer-EBPP[$A_1G_4I_1$]$_6$-HPC5. The size of the AuNPs was about 10 nm, which coincided with the reported cavity radius of HPC. For assessment of the AuNP-anti-Flt1-HPC4-EBPP[$A_1G_4I_1$]$_6$-PEDF 34-mer-EBPP[$A_1G_4I_1$]$_6$-HPC5 composite as a Raman probe, MGITC (malachite green isothiocyanate) was introduced to the AuNP surface using the pH responsiveness of HPC as a Raman dye. HPC has reversible pH responsiveness. Its structure is disrupted under acidic conditions, and is restored to the original structure at natural pH. The HPC of the AuNP-anti-Flt1-HPC4-EBPP[$A_1G_4I_1$]$_6$-PEDF 34-mer-EBPP[$A_1G_4I_1$]$_6$-HPC5 composite became loose as pH was decreased to 6 for introduction of MGITC to the AuNP surface, and recovered its structure as pH was adjusted to 7.4. The AuNP-anti-Flt1-HPC4-EBPP[$A_1G_4I_1$]$_6$-PEDF 34-mer-EBPP[$A_1G_4I_1$]$_6$-HPC5 composite incubated with 10 nM MGITC showed a significant Raman spectrum as shown in FIG. 6 (D). The potential of anti-Flt1-HPC4-EBPP[$A_1G_4I_1$]$_6$-PEDF 34-mer-EBPP[$A_1G_4I_1$]$_6$-HPC5 for cell imaging and as a Raman probe was verified from the HUVEC imaging and Raman spectrum.

The anti-Flt1-HPC4-EBPP[$A_1G_4I_1$]$_6$-PEDF 34-mer-EBPP[$A_1G_4I_1$]$_6$-HPC5, which is a fusion protein cage having a multivalent peptide for inhibiting angiogenesis, was controlled precisely at genetic level in order to expose anti-Flt1 peptide and PEDF 34-mer, which are anti-angiogenic peptides, without interfering with self-assembly to a cage structure. The two anti-angiogenic peptides, anti-Flt1 peptide and PEDF 34-mer, had different mechanisms for inhibition of angiogenesis, which are related with intracellular signaling. The anti-Flt1-peptide inhibited intracellular signaling for angiogenesis, and the PEDF 34-mer induced anti-angiogenic signals. These different mechanisms affected the administration dosage of the fusion protein cage in in-vitro tube formation assay. In in-vitro tube formation assay of HUVECs, the fusion protein cage decreased tube formation of HUVECs gradually as the concentration of the anti-angiogenic peptide was increased. Whereas the fusion protein cage having the anti-Flt1 peptide showed anti-angiogenic effect in µM ranges, the fusion protein cage having the PEDF 34-mer inhibited the tube formation of HUVECs in nM ranges. The anti-Flt1-HPC4-EBPP[$A_1G_4I_1$]$_6$-PEDF 34-mer-EBPP[$A_1G_4I_1$]$_6$-HPC5 fusion protein cage including the two anti-angiogenic peptides showed the highest inhibitory effect in a broad concentration range. The fluorescent dye-conjugated anti-Flt1-HPC4-EBPP[$A_1G_4I_1$]$_6$-PEDF 34-mer-EBPP[$A_1G_4I_1$]$_6$-HPC5 showed capability as a cell imaging probe for inhibition of cell extension investigated by HUVEC imaging. The AuNP-anti-Flt1-HPC4-EBPP[$A_1G_4I_1$]$_6$-PEDF 34-mer-EBPP[$A_1G_4I_1$]$_6$-HPC5 exhibited Raman spectra after introduction of MGITC to AuNP surface. The fusion protein cage including two different anti-angiogenic peptide and HPC according to the present disclosure has a remarkable potential as a therapeutic peptide for against angiogenesis and for tracing the progress of angiogenesis-related diseases.

Fusion of self-assembled protein nanostructures with functional peptides has been studied for application in theranostics and nanomedicine. In the present disclosure, a fusion polypeptide consisting of a vascular endothelial growth factor receptor (VEGFR)-targeting peptide, a pigment epithelium-derived factor (PEDF) 34-mer peptide for inhibiting angiogenesis, a temperature-responsive elastin-based polypeptide (EBP) and a helix-based protein cage (HPC) was prepared by a genetic engineering technique, which was then overexpressed in E. coli and purified by a non-chromatographic inverse transition cycling (ITC) method. The VEGFR-target peptide and the anti-angiogenic PEDF 34-mer peptide were exposed in the self-assembled protein cage and the EBP was introduced as a non-chromatographic purification tag. The physical and chemical properties and DySA (dynamic self-assembly) of the fusion protein cage having the multivalent peptide for inhibiting angiogenesis were characterized. The fusion protein cage inhibited the migration and tube formation of human umbilical vein endothelial cells (HUVECs) on Matrigel, which showed possibility as a nanoscale biomedicine for inhibiting angiogenesis. The fusion protein cage having anti-angiogenic effect was prepared into a fluorescent nanoprobe or an inorganic-organic hybrid SERS nanoprobe by chemically conjugating a fluorescent dye to the protein cage or metal nanoparticles (MNPs). For example, gold, silver, copper or iron nanoparticles may be chemically conjugated with a Raman dye for labeling in applications to theranostics and nanomedicine. The fusion protein cage having a multivalent peptide for inhibiting angiogenesis according to present disclosure may be used as a therapeutic agent for uncontrolled retinal, corneal and choroidal neovascularization, tumor growth, cancer cell metastasis, diabetic retinopathy and asthma and for bioimaging and biosensing of the progress thereof in the field of theranostics and nanomedicine.

The invention claimed is:

1. A fusion polypeptide for inhibiting angiogenesis,
    i) consisting of an anti-angiogenic peptide; a helix-based polypeptide represented by SEQ ID NO 1, which is linked to the peptide; a hydrophilic elastin-based polypeptide (hydrophilic EBP) linked to the helix-based peptide; and a helix-based polypeptide represented by SEQ ID NO 2, which is linked to the hydrophilic EBP,
    ii) consisting of a helix-based polypeptide represented by SEQ ID NO 1; a first hydrophilic EBP linked to the peptide; an anti-angiogenic peptide linked to the first hydrophilic EBP; a second hydrophilic EBP linked to the anti-angiogenic peptide; and a helix-based polypeptide represented by SEQ ID NO 2, which is linked to the second hydrophilic EBP, or
    iii) consisting of an anti-angiogenic peptide; a helix-based polypeptide represented by SEQ ID NO 1, which is linked to the peptide; a hydrophilic EBP linked to the helix-based polypeptide; an anti-angiogenic peptide linked to the hydrophilic EBP; a hydrophilic EBP linked to the anti-angiogenic peptide; and a helix-based polypeptide represented by SEQ ID NO 2, which is linked to the hydrophilic EBP.

2. The fusion polypeptide for inhibiting angiogenesis of claim 1, wherein the anti-angiogenic peptide is an anti-Flt1 peptide [SEQ ID NO 3] or a PEDF (pigment epithelial-derived factor) 34-mer [SEQ ID NO 4].

3. The fusion polypeptide for inhibiting angiogenesis of claim 1, wherein the hydrophilic EBP is represented by one of SEQ ID NOS 5 to 14.

4. The fusion polypeptide for inhibiting angiogenesis of claim 1, wherein the i) consists of [anti-Flt1 peptide of SEQ ID NO 3]-[helix-based polypeptide represented by SEQ ID NO 1]-[hydrophilic EBP]-[helix-based polypeptide represented by SEQ ID NO 2].

5. The fusion polypeptide for inhibiting angiogenesis of claim 1, wherein the ii) consists of [helix-based polypeptide represented by SEQ ID NO 1]-[hydrophilic EBP]-[EDF 34-mer of SEQ ID NO 4]-[hydrophilic EBP]-[helix-based polypeptide represented by SEQ ID NO 2].

6. The fusion polypeptide for inhibiting angiogenesis of claim 1, wherein the iii) consists of [anti-Flt1 peptide of SEQ ID NO 3]-[helix-based polypeptide represented by SEQ ID NO 1]-[hydrophilic EBP]-[EDF 34-mer of SEQ ID NO 4]-[hydrophilic EBP]-[helix-based polypeptide represented by SEQ ID NO 2].

7. The fusion polypeptide for inhibiting angiogenesis of claim 1, wherein the i) is represented by SEQ ID NO 16, the ii) is represented by SEQ ID NO 17, and the iii) is represented by SEQ ID NO 18.

8. A composition for treating a disease caused by angiogenesis, comprising the fusion polypeptide for inhibiting angiogenesis according to claim 1.

9. The composition for treating a disease caused by angiogenesis of claim 8, wherein the disease caused by angiogenesis is one or more selected from a group consisting of diabetic retinopathy, retinopathy of prematurity, macular degeneration, choroidal neovascularization, neovascular glaucoma, ocular disease caused by corneal neovascularization, corneal transplantation rejection, corneal edema, corneal opacity, cancer, hemangioma, angiofibroma, rheumatoid arthritis and psoriasis.

10. A fusion protein nanocage having a peptide for inhibiting angiogenesis, prepared as the helix-based polypeptide represented by SEQ ID NO 1 and the helix-based polypeptide represented by SEQ ID NO 2 in the fusion polypeptide for inhibiting angiogenesis according to claim 1 self-assemble.

11. The fusion protein nanocage having a peptide for inhibiting angiogenesis of claim 10, wherein the nanocage has a multivalent fusion polypeptide for inhibiting angiogenesis.

12. A theranostic nanoprobe for a disease caused by angiogenesis, comprising:
    a fluorescent dye; and
    the fusion protein nanocage having a peptide for inhibiting angiogenesis according to claim 10,
    wherein the fluorescent dye is held in the nanocage.

13. A theranostic nanoprobe for a disease caused by angiogenesis, comprising:
    a Raman dye-bound metal nanoparticle; and
    the fusion protein nanocage having a peptide for inhibiting angiogenesis according to claim 10,
    wherein the Raman dye-bound metal nanoparticle is held in the nanocage.

14. The theranostic nanoprobe of claim 12, wherein the disease caused by angiogenesis is one or more selected from a group consisting of diabetic retinopathy, retinopathy of prematurity, macular degeneration, choroidal neovascularization, neovascular glaucoma, ocular disease caused by corneal neovascularization, corneal transplantation rejection, corneal edema, corneal opacity, cancer, hemangioma, angiofibroma, rheumatoid arthritis and psoriasis.

15. The theranostic nanoprobe of claim 13, wherein the disease caused by angiogenesis is one or more selected from a group consisting of diabetic retinopathy, retinopathy of prematurity, macular degeneration, choroidal neovascularization, neovascular glaucoma, ocular disease caused by corneal neovascularization, corneal transplantation rejection, corneal edema, corneal opacity, cancer, hemangioma, angiofibroma, rheumatoid arthritis and psoriasis.

* * * * *

SEQUENCE LISTING

<160> NUMBER OF SEQ ID NOS: 28

<210> SEQ ID NO 1
<211> LENGTH: 156
<212> TYPE: PRT
<213> ORGANISM: Artificial Sequence
<220> FEATURE:
<223> OTHER INFORMATION: helix-based protein cage

```
<400> SEQUENCE: 1

Ser Ser Gln Ile Arg Gln Asn Tyr Ser Thr Asp Val Glu Ala Ala Val
1               5                   10                  15

Asn Ser Leu Val Asn Leu Tyr Leu Gln Ala Ser Tyr Thr Tyr Leu Ser
            20                  25                  30

Leu Gly Phe Tyr Phe Asp Arg Asp Asp Val Ala Leu Glu Gly Val Ser
        35                  40                  45

His Phe Phe Arg Glu Leu Ala Glu Glu Lys Arg Glu Gly Tyr Glu Arg
    50                  55                  60

Leu Leu Lys Met Gln Asn Gln Arg Gly Gly Arg Ala Leu Phe Gln Asp
65                  70                  75                  80

Ile Lys Lys Pro Ala Glu Asp Glu Trp Gly Lys Thr Pro Asp Ala Met
                85                  90                  95

Lys Ala Ala Met Ala Leu Glu Lys Lys Leu Asn Gln Ala Leu Leu Asp
            100                 105                 110

Leu His Ala Leu Gly Ser Ala Arg Thr Asp Pro His Leu Cys Asp Phe
        115                 120                 125

Leu Glu Thr His Phe Leu Asp Glu Glu Val Lys Leu Ile Lys Lys Met
    130                 135                 140

Gly Asp His Leu Thr Asn Leu His Arg Leu Gly Gly
145                 150                 155

<210> SEQ ID NO 2
<211> LENGTH: 18
<212> TYPE: PRT
<213> ORGANISM: Artificial Sequence
<220> FEATURE:
<223> OTHER INFORMATION: helix-based protein cage

<400> SEQUENCE: 2

Pro Glu Ala Gly Leu Gly Glu Tyr Leu Phe Glu Arg Leu Thr Leu Lys
1               5                   10                  15

His Asp

<210> SEQ ID NO 3
<211> LENGTH: 6
<212> TYPE: PRT
<213> ORGANISM: Artificial Sequence
<220> FEATURE:
<223> OTHER INFORMATION: Anti-Flt1 peptide

<400> SEQUENCE: 3

Gly Asn Gln Trp Phe Ile
1               5

<210> SEQ ID NO 4
<211> LENGTH: 34
<212> TYPE: PRT
<213> ORGANISM: Artificial Sequence
<220> FEATURE:
<223> OTHER INFORMATION: Elastin-based peptide

<400> SEQUENCE: 4

Asp Pro Phe Phe Lys Val Pro Val Asn Lys Leu Ala Ala Ala Val Ser
1               5                   10                  15

Asn Phe Gly Tyr Asp Leu Tyr Arg Val Arg Ser Ser Thr Ser Pro Thr
            20                  25                  30

Thr Asn
```

```
<210> SEQ ID NO 5
<211> LENGTH: 30
<212> TYPE: PRT
<213> ORGANISM: Artificial Sequence
<220> FEATURE:
<223> OTHER INFORMATION: Elastin-based peptide

<400> SEQUENCE: 5

Val Pro Gly Gly Gly Val Pro Gly Ala Gly Val Pro Gly Gly Val
1               5                   10                  15

Pro Gly Gly Gly Val Pro Gly Ile Gly Val Pro Gly Gly Gly
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Elastin-based peptide

<400> SEQUENCE: 6

Val Pro Ala Gly Gly Val Pro Ala Ala Gly Val Pro Ala Gly Val
1               5                   10                  15

Pro Ala Gly Gly Val Pro Ala Ile Gly Val Pro Ala Gly Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: helix-based protein cage

<400> SEQUENCE: 7

Val Pro Gly Gly Gly Val Pro Gly Lys Gly Val Pro Gly Gly Val
1               5                   10                  15

Pro Gly Gly Gly Val Pro Gly Ile Gly Val Pro Gly Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Elastin-based peptide

<400> SEQUENCE: 8

Val Pro Ala Gly Gly Val Pro Ala Lys Gly Val Pro Ala Gly Val
1               5                   10                  15

Pro Ala Gly Gly Val Pro Ala Ile Gly Val Pro Ala Gly Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Elastin-based peptide

<400> SEQUENCE: 9

Val Pro Gly Gly Gly Val Pro Gly Asp Gly Val Pro Gly Gly Val
1               5                   10                  15

Pro Gly Gly Gly Val Pro Gly Ile Gly Val Pro Gly Gly Gly
            20                  25                  30
```

```
<210> SEQ ID NO 10
<211> LENGTH: 30
<212> TYPE: PRT
<213> ORGANISM: Artificial Sequence
<220> FEATURE:
<223> OTHER INFORMATION: Elastin-based peptide

<400> SEQUENCE: 10

Val Pro Ala Gly Gly Val Pro Ala Asp Gly Val Pro Ala Gly Gly Val
1               5                  10                  15

Pro Ala Gly Gly Val Pro Ala Ile Gly Val Pro Ala Gly Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Elastin-based peptide

<400> SEQUENCE: 11

Val Pro Gly Gly Gly Val Pro Gly Glu Gly Val Pro Gly Gly Gly Val
1               5                  10                  15

Pro Gly Gly Gly Val Pro Gly Ile Gly Val Pro Gly Gly Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Elastin-based peptide

<400> SEQUENCE: 12

Val Pro Ala Gly Gly Val Pro Ala Glu Gly Val Pro Ala Gly Gly Val
1               5                  10                  15

Pro Ala Gly Gly Val Pro Ala Ile Gly Val Pro Ala Gly Gly
            20                  25                  30

<210> SEQ ID NO 13
<211> LENGTH: 6
<212> TYPE: PRT
<213> ORGANISM: Artificial Sequence
<220> FEATURE:
<223> OTHER INFORMATION: Elastin-based peptide

<400> SEQUENCE: 13

Gly Asn Gln Trp Phe Ile
1               5

<210> SEQ ID NO 14
<211> LENGTH: 360
<212> TYPE: PRT
<213> ORGANISM: Artificial Sequence
<220> FEATURE:
<223> OTHER INFORMATION: Elastin-based peptide

<400> SEQUENCE: 14

Val Pro Ala Gly Gly Val Pro Ala Ala Gly Val Pro Ala Gly Gly Val
1               5                  10                  15

Pro Ala Gly Gly Val Pro Ala Ile Gly Val Pro Ala Gly Gly Val Pro
            20                  25                  30

Ala Gly Gly Val Pro Ala Ala Gly Val Pro Ala Gly Gly Val Pro Ala
```

```
                35                  40                  45
Gly Gly Val Pro Ala Ile Gly Val Pro Ala Gly Gly Val Pro Ala Gly
 50                  55                  60
Pro Val Pro Ala Ala Gly Val Pro Ala Gly Gly Val Pro Ala Gly Gly
 65                  70                  75                  80
Val Pro Ala Ile Gly Val Pro Ala Gly Gly Val Pro Ala Gly Gly Val
                 85                  90                  95
Pro Ala Ala Gly Val Pro Ala Gly Gly Val Pro Ala Gly Gly Val Pro
                100                 105                 110
Ala Ile Gly Val Pro Ala Gly Gly Val Pro Ala Gly Gly Val Pro Ala
            115                 120                 125
Ala Gly Val Pro Ala Gly Gly Val Pro Ala Gly Gly Val Pro Ala Ile
        130                 135                 140
Gly Val Pro Ala Gly Gly Val Pro Ala Gly Gly Val Pro Ala Ala Gly
145                 150                 155                 160
Val Pro Ala Gly Gly Val Pro Ala Gly Gly Val Pro Ala Ile Gly Val
                165                 170                 175
Pro Ala Gly Gly Val Pro Ala Gly Gly Val Pro Ala Ala Gly Val Pro
            180                 185                 190
Ala Gly Gly Val Pro Ala Gly Gly Val Pro Ala Ile Gly Val Pro Ala
        195                 200                 205
Gly Gly Val Pro Ala Gly Gly Val Pro Ala Ala Gly Val Pro Ala Gly
210                 215                 220
Gly Val Pro Ala Gly Gly Val Pro Ala Ile Gly Val Pro Ala Gly Gly
225                 230                 235                 240
Val Pro Ala Gly Gly Val Pro Ala Ala Gly Val Pro Ala Gly Gly Val
                245                 250                 255
Pro Ala Gly Gly Val Pro Ala Ile Gly Val Pro Ala Gly Gly Val Pro
            260                 265                 270
Ala Gly Gly Val Pro Ala Ala Gly Val Pro Ala Gly Gly Val Pro Ala
        275                 280                 285
Gly Gly Val Pro Ala Ile Gly Val Pro Ala Gly Gly Val Pro Ala Gly
290                 295                 300
Gly Val Pro Ala Ala Gly Val Pro Ala Gly Gly Val Pro Ala Gly Gly
305                 310                 315                 320
Val Pro Ala Ile Gly Val Pro Ala Gly Gly Val Pro Ala Gly Gly Val
                325                 330                 335
Pro Ala Ala Gly Val Pro Ala Gly Gly Val Pro Ala Gly Gly Val Pro
            340                 345                 350
Ala Ile Gly Val Pro Ala Gly Gly
        355                 360
```

<210> SEQ ID NO 15
<211> LENGTH: 534
<212> TYPE: PRT
<213> ORGANISM: Artificial Sequence
<220> FEATURE:
<223> OTHER INFORMATION: HPC4-EBPP[A1G4I1]12-HPC5

<400> SEQUENCE: 15

```
Ser Ser Gln Ile Arg Gln Asn Tyr Ser Thr Asp Val Glu Ala Ala Val
  1               5                  10                  15
Asn Ser Leu Val Asn Leu Tyr Leu Gln Ala Ser Tyr Thr Tyr Leu Ser
             20                  25                  30
Leu Gly Phe Tyr Phe Asp Arg Asp Asp Val Ala Leu Glu Gly Val Ser
```

```
                35                  40                  45
His Phe Phe Arg Glu Leu Ala Glu Glu Lys Arg Glu Gly Tyr Glu Arg
 50                  55                  60

Leu Leu Lys Met Gln Asn Gln Arg Gly Gly Arg Ala Leu Phe Gln Asp
 65                  70                  75                  80

Ile Lys Lys Pro Ala Glu Asp Glu Trp Gly Lys Thr Pro Asp Ala Met
                 85                  90                  95

Lys Ala Ala Met Ala Leu Glu Lys Lys Leu Asn Gln Ala Leu Leu Asp
                100                 105                 110

Leu His Ala Leu Gly Ser Ala Arg Thr Asp Pro His Leu Cys Asp Phe
            115                 120                 125

Leu Glu Thr His Phe Leu Asp Glu Glu Val Lys Leu Ile Lys Lys Met
        130                 135                 140

Gly Asp His Leu Thr Asn Leu His Arg Leu Gly Gly Val Pro Ala Gly
145                 150                 155                 160

Gly Val Pro Ala Ala Gly Val Pro Ala Gly Gly Val Pro Ala Gly Gly
                165                 170                 175

Val Pro Ala Ile Gly Val Pro Ala Gly Gly Val Pro Ala Gly Gly Val
            180                 185                 190

Pro Ala Ala Gly Val Pro Ala Gly Gly Val Pro Ala Gly Gly Val Pro
        195                 200                 205

Ala Ile Gly Val Pro Ala Gly Gly Val Pro Ala Gly Gly Val Pro Ala
    210                 215                 220

Ala Gly Val Pro Ala Gly Gly Val Pro Ala Gly Gly Val Pro Ala Ile
225                 230                 235                 240

Gly Val Pro Ala Gly Gly Val Pro Ala Gly Gly Val Pro Ala Ala Gly
                245                 250                 255

Val Pro Ala Gly Gly Val Pro Ala Gly Gly Val Pro Ala Ile Gly Val
            260                 265                 270

Pro Ala Gly Gly Val Pro Ala Gly Gly Val Pro Ala Ala Gly Val Pro
        275                 280                 285

Ala Gly Gly Val Pro Ala Gly Gly Val Pro Ala Ile Gly Val Pro Ala
    290                 295                 300

Gly Gly Val Pro Ala Gly Gly Val Pro Ala Ala Gly Val Pro Ala Gly
305                 310                 315                 320

Gly Val Pro Ala Gly Gly Val Pro Ala Ile Gly Val Pro Ala Gly Gly
                325                 330                 335

Val Pro Ala Gly Gly Val Pro Ala Ala Gly Val Pro Ala Gly Gly Val
            340                 345                 350

Pro Ala Gly Gly Val Pro Ala Ile Gly Val Pro Ala Gly Gly Val Pro
        355                 360                 365

Ala Gly Gly Val Pro Ala Ala Gly Val Pro Ala Gly Gly Val Pro Ala
    370                 375                 380

Gly Gly Val Pro Ala Ile Gly Val Pro Ala Gly Gly Val Pro Ala Gly
385                 390                 395                 400

Gly Val Pro Ala Ala Gly Val Pro Ala Gly Gly Val Pro Ala Gly Gly
                405                 410                 415

Val Pro Ala Ile Gly Val Pro Ala Gly Gly Val Pro Ala Gly Gly Val
            420                 425                 430

Pro Ala Ala Gly Val Pro Ala Gly Gly Val Pro Ala Gly Gly Val Pro
        435                 440                 445

Ala Ile Gly Val Pro Ala Gly Gly Val Pro Ala Gly Gly Val Pro Ala
    450                 455                 460
```

-continued

```
Ala Gly Val Pro Ala Gly Gly Val Pro Ala Gly Gly Val Pro Ala Ile
465                 470                 475                 480

Gly Val Pro Ala Gly Gly Val Pro Ala Gly Gly Val Pro Ala Ala Gly
                485                 490                 495

Val Pro Ala Gly Gly Val Pro Ala Gly Gly Val Pro Ala Ile Gly Val
            500                 505                 510

Pro Ala Gly Gly Pro Glu Ala Gly Leu Gly Glu Tyr Leu Phe Glu Arg
        515                 520                 525

Leu Thr Leu Lys His Asp
    530

<210> SEQ ID NO 16
<211> LENGTH: 540
<212> TYPE: PRT
<213> ORGANISM: Artificial Sequence
<220> FEATURE:
<223> OTHER INFORMATION: Anti-Flt1-HPC4-EBpppA1G4I1]12-HPC5

<400> SEQUENCE: 16

Gly Asn Gln Trp Phe Ile Ser Ser Gln Ile Arg Gln Asn Tyr Ser Thr
1               5                   10                  15

Asp Val Glu Ala Ala Val Asn Ser Leu Val Asn Leu Tyr Leu Gln Ala
            20                  25                  30

Ser Tyr Thr Tyr Leu Ser Leu Gly Phe Tyr Phe Asp Arg Asp Asp Val
        35                  40                  45

Ala Leu Glu Gly Val Ser His Phe Phe Arg Glu Leu Ala Glu Glu Lys
    50                  55                  60

Arg Glu Gly Tyr Glu Arg Leu Leu Lys Met Gln Asn Gln Arg Gly Gly
65                  70                  75                  80

Arg Ala Leu Phe Gln Asp Ile Lys Lys Pro Ala Glu Asp Glu Trp Gly
                85                  90                  95

Lys Thr Pro Asp Ala Met Lys Ala Ala Met Ala Leu Glu Lys Lys Leu
            100                 105                 110

Asn Gln Ala Leu Leu Asp Leu His Ala Leu Gly Ser Ala Arg Thr Asp
        115                 120                 125

Pro His Leu Cys Asp Phe Leu Glu Thr His Phe Leu Asp Glu Glu Val
    130                 135                 140

Lys Leu Ile Lys Lys Met Gly Asp His Leu Thr Asn Leu His Arg Leu
145                 150                 155                 160

Gly Gly Val Pro Ala Gly Gly Val Pro Ala Ala Gly Val Pro Ala Gly
                165                 170                 175

Gly Val Pro Ala Gly Gly Val Pro Ala Ile Gly Val Pro Ala Gly Gly
            180                 185                 190

Val Pro Ala Gly Gly Val Pro Ala Ala Gly Val Pro Ala Gly Gly Val
        195                 200                 205

Pro Ala Gly Gly Val Pro Ala Ile Gly Val Pro Ala Gly Gly Val Pro
    210                 215                 220

Ala Gly Gly Val Pro Ala Ala Gly Val Pro Ala Gly Gly Val Pro Ala
225                 230                 235                 240

Gly Gly Val Pro Ala Ile Gly Val Pro Ala Gly Gly Val Pro Ala Gly
                245                 250                 255

Gly Val Pro Ala Ala Gly Val Pro Ala Gly Gly Val Pro Ala Gly Gly
            260                 265                 270

Val Pro Ala Ile Gly Val Pro Ala Gly Gly Val Pro Ala Gly Gly Val
        275                 280                 285
```

Pro Ala Gly Val Pro Ala Gly Gly Val Pro Ala Gly Gly Val Pro
    290                 295                 300

Ala Ile Gly Val Pro Ala Gly Gly Val Pro Ala Gly Gly Val Pro Ala
305                 310                 315                 320

Ala Gly Val Pro Ala Gly Gly Val Pro Ala Gly Gly Val Pro Ala Ile
            325                 330                 335

Gly Val Pro Ala Gly Gly Val Pro Ala Gly Gly Val Pro Ala Ala Gly
        340                 345                 350

Val Pro Ala Gly Gly Val Pro Ala Gly Gly Val Pro Ala Ile Gly Val
    355                 360                 365

Pro Ala Gly Gly Val Pro Ala Gly Gly Val Pro Ala Ala Gly Val Pro
    370                 375                 380

Ala Gly Gly Val Pro Ala Gly Gly Val Pro Ala Ile Gly Val Pro Ala
385                 390                 395                 400

Gly Gly Val Pro Ala Gly Gly Val Pro Ala Ala Gly Val Pro Ala Gly
            405                 410                 415

Gly Val Pro Ala Gly Gly Val Pro Ala Ile Gly Val Pro Ala Gly Gly
        420                 425                 430

Val Pro Ala Gly Gly Val Pro Ala Ala Gly Val Pro Ala Gly Gly Val
    435                 440                 445

Pro Ala Gly Gly Val Pro Ala Ile Gly Val Pro Ala Gly Gly Val Pro
    450                 455                 460

Ala Gly Gly Val Pro Ala Ala Gly Val Pro Ala Gly Gly Val Pro Ala
465                 470                 475                 480

Gly Gly Val Pro Ala Ile Gly Val Pro Ala Gly Gly Val Pro Ala Gly
            485                 490                 495

Gly Val Pro Ala Ala Gly Val Pro Ala Gly Gly Val Pro Ala Gly Gly
        500                 505                 510

Val Pro Ala Ile Gly Val Pro Ala Gly Gly Pro Glu Ala Gly Leu Gly
    515                 520                 525

Glu Tyr Leu Phe Glu Arg Leu Thr Leu Lys His Asp
    530                 535                 540

<210> SEQ ID NO 17
<211> LENGTH: 568
<212> TYPE: PRT
<213> ORGANISM: Artificial Sequence
<220> FEATURE:
<223> OTHER INFORMATION: HPC4-EBPP[A1G4I1]6-PEDF
      34-mer-EBPP[A1G4I1]6-HPC5

<400> SEQUENCE: 17

Ser Ser Gln Ile Arg Gln Asn Tyr Ser Thr Asp Val Glu Ala Ala Val
1               5                   10                  15

Asn Ser Leu Val Asn Leu Tyr Leu Gln Ala Ser Tyr Thr Tyr Leu Ser
            20                  25                  30

Leu Gly Phe Tyr Phe Asp Arg Asp Asp Val Ala Leu Glu Gly Val Ser
        35                  40                  45

His Phe Phe Arg Glu Leu Ala Glu Glu Lys Arg Glu Gly Tyr Glu Arg
    50                  55                  60

Leu Leu Lys Met Gln Asn Gln Arg Gly Gly Arg Ala Leu Phe Gln Asp
65                  70                  75                  80

Ile Lys Lys Pro Ala Glu Asp Glu Trp Gly Lys Thr Pro Asp Ala Met
                85                  90                  95

Lys Ala Ala Met Ala Leu Glu Lys Lys Leu Asn Gln Ala Leu Leu Asp

```
              100                 105                 110
Leu His Ala Leu Gly Ser Ala Arg Thr Asp Pro His Leu Cys Asp Phe
            115                 120                 125
Leu Glu Thr His Phe Leu Asp Glu Val Lys Leu Ile Lys Lys Met
            130                 135             140
Gly Asp His Leu Thr Asn Leu His Arg Leu Gly Val Pro Ala Gly
145                 150                 155                 160
Gly Val Pro Ala Ala Gly Val Pro Ala Gly Gly Val Pro Ala Gly Gly
                165                 170                 175
Val Pro Ala Ile Gly Val Pro Ala Gly Gly Val Pro Ala Gly Gly Val
            180                 185                 190
Pro Ala Ala Gly Val Pro Ala Gly Gly Val Pro Ala Gly Gly Val Pro
        195                 200                 205
Ala Ile Gly Val Pro Ala Gly Gly Val Pro Ala Gly Gly Val Pro Ala
        210                 215                 220
Ala Gly Val Pro Ala Gly Gly Val Pro Ala Gly Gly Val Pro Ala Ile
225                 230                 235                 240
Gly Val Pro Ala Gly Gly Val Pro Ala Gly Gly Val Pro Ala Ala Gly
                245                 250                 255
Val Pro Ala Gly Gly Val Pro Ala Gly Gly Val Pro Ala Ile Gly Val
            260                 265                 270
Pro Ala Gly Gly Val Pro Ala Gly Gly Val Pro Ala Ala Gly Val Pro
            275                 280                 285
Ala Gly Gly Val Pro Ala Gly Gly Val Pro Ala Ile Gly Val Pro Ala
        290                 295                 300
Gly Gly Val Pro Ala Gly Gly Val Pro Ala Ala Gly Val Pro Ala Gly
305                 310                 315                 320
Gly Val Pro Ala Gly Gly Val Pro Ala Ile Gly Val Pro Ala Gly Gly
                325                 330                 335
Asp Pro Phe Phe Lys Val Pro Val Asn Lys Leu Ala Ala Ala Val Ser
            340                 345                 350
Asn Phe Gly Tyr Asp Leu Tyr Arg Val Arg Ser Ser Thr Ser Pro Thr
            355                 360                 365
Thr Asn Val Pro Ala Gly Gly Val Pro Ala Ala Gly Val Pro Ala Gly
            370                 375             380
Gly Val Pro Ala Gly Gly Val Pro Ala Ile Gly Val Pro Ala Gly Gly
385                 390                 395                 400
Val Pro Ala Gly Gly Val Pro Ala Ala Gly Val Pro Ala Gly Gly Val
                405                 410                 415
Pro Ala Gly Gly Val Pro Ala Ile Gly Val Pro Ala Gly Gly Val Pro
            420                 425                 430
Ala Gly Gly Val Pro Ala Ala Gly Val Pro Ala Gly Gly Val Pro Ala
        435                 440                 445
Gly Gly Val Pro Ala Ile Gly Val Pro Ala Gly Gly Val Pro Ala Gly
450                 455                 460
Gly Val Pro Ala Ala Gly Val Pro Ala Gly Gly Val Pro Ala Gly Gly
465                 470                 475                 480
Val Pro Ala Ile Gly Val Pro Ala Gly Gly Val Pro Ala Gly Gly Val
            485                 490                 495
Pro Ala Ala Gly Val Pro Ala Gly Gly Val Pro Ala Gly Gly Val Pro
            500                 505                 510
Ala Ile Gly Val Pro Ala Gly Gly Val Pro Ala Gly Gly Val Pro Ala
        515                 520                 525
```

Ala Gly Val Pro Ala Gly Gly Val Pro Ala Gly Gly Val Pro Ala Ile
        530                 535                 540

Gly Val Pro Ala Gly Gly Pro Glu Ala Gly Leu Gly Glu Tyr Leu Phe
545                 550                 555                 560

Glu Arg Leu Thr Leu Lys His Asp
                565

<210> SEQ ID NO 18
<211> LENGTH: 574
<212> TYPE: PRT
<213> ORGANISM: Artificial Sequence
<220> FEATURE:
<223> OTHER INFORMATION: Anti-Flt1-HPC4- EBPP[A1G4I1]6-PEDF
      34-mer-EBPP[A1G4I1]6-HPC5

<400> SEQUENCE: 18

Gly Asn Gln Trp Phe Ile Ser Ser Gln Ile Arg Gln Asn Tyr Ser Thr
1               5                   10                  15

Asp Val Glu Ala Ala Val Asn Ser Leu Val Asn Leu Tyr Leu Gln Ala
            20                  25                  30

Ser Tyr Thr Tyr Leu Ser Leu Gly Phe Tyr Phe Asp Arg Asp Asp Val
        35                  40                  45

Ala Leu Glu Gly Val Ser His Phe Phe Arg Glu Leu Ala Glu Glu Lys
50                  55                  60

Arg Glu Gly Tyr Glu Arg Leu Leu Lys Met Gln Asn Gln Arg Gly Gly
65                  70                  75                  80

Arg Ala Leu Phe Gln Asp Ile Lys Lys Pro Ala Glu Asp Glu Trp Gly
                85                  90                  95

Lys Thr Pro Asp Ala Met Lys Ala Ala Met Ala Leu Glu Lys Lys Leu
            100                 105                 110

Asn Gln Ala Leu Leu Asp Leu His Ala Leu Gly Ser Ala Arg Thr Asp
        115                 120                 125

Pro His Leu Cys Asp Phe Leu Glu Thr His Phe Leu Asp Glu Glu Val
    130                 135                 140

Lys Leu Ile Lys Lys Met Gly Asp His Leu Thr Asn Leu His Arg Leu
145                 150                 155                 160

Gly Gly Val Pro Ala Gly Val Pro Ala Ala Gly Val Pro Ala Gly Gly
                165                 170                 175

Val Pro Ala Gly Gly Val Pro Ala Ile Gly Val Pro Ala Gly Gly
            180                 185                 190

Val Pro Ala Gly Gly Val Pro Ala Ala Gly Val Pro Ala Gly Gly Val
        195                 200                 205

Pro Ala Gly Gly Val Pro Ala Ile Gly Val Pro Ala Gly Gly Val Pro
    210                 215                 220

Ala Gly Gly Val Pro Ala Ala Gly Val Pro Ala Gly Gly Val Pro Ala
225                 230                 235                 240

Gly Gly Val Pro Ala Ile Gly Val Pro Ala Gly Gly Val Pro Ala Gly
                245                 250                 255

Gly Val Pro Ala Ala Gly Val Pro Ala Gly Gly Val Pro Ala Gly Gly
            260                 265                 270

Val Pro Ala Ile Gly Val Pro Ala Gly Gly Val Pro Ala Gly Gly Val
        275                 280                 285

Pro Ala Ala Gly Val Pro Ala Gly Gly Val Pro Ala Gly Gly Val Pro
    290                 295                 300

Ala Ile Gly Val Pro Ala Gly Gly Val Pro Ala Gly Gly Val Pro Ala 305                 310                 315                 320
Ala Gly Val Pro Ala Gly Gly Val Pro Ala Gly Gly Val Pro Ala Ile
                325                 330                 335

Gly Val Pro Ala Gly Gly Asp Pro Phe Phe Lys Val Pro Val Asn Lys
            340                 345                 350

Leu Ala Ala Ala Val Ser Asn Phe Gly Tyr Asp Leu Tyr Arg Val Arg
        355                 360                 365

Ser Ser Thr Ser Pro Thr Thr Asn Val Pro Ala Gly Gly Val Pro Ala
    370                 375                 380

Ala Gly Val Pro Ala Gly Gly Val Pro Ala Gly Gly Val Pro Ala Ile
385                 390                 395                 400

Gly Val Pro Ala Gly Gly Val Pro Ala Gly Gly Val Pro Ala Ala Gly
                405                 410                 415

Val Pro Ala Gly Gly Val Pro Ala Gly Gly Val Pro Ala Ile Gly Val
                420                 425                 430

Pro Ala Gly Gly Val Pro Ala Gly Gly Val Pro Ala Ala Gly Val Pro
                435                 440                 445

Ala Gly Gly Val Pro Ala Gly Gly Val Pro Ala Ile Gly Val Pro Ala
        450                 455                 460

Gly Gly Val Pro Ala Gly Gly Val Pro Ala Ala Gly Val Pro Ala Gly
465                 470                 475                 480

Gly Val Pro Ala Gly Gly Val Pro Ala Ile Gly Val Pro Ala Gly Gly
                485                 490                 495

Val Pro Ala Gly Gly Val Pro Ala Ala Gly Val Pro Ala Gly Gly Val
            500                 505                 510

Pro Ala Gly Gly Val Pro Ala Ile Gly Val Pro Ala Gly Gly Val Pro
            515                 520                 525

Ala Gly Gly Val Pro Ala Ala Gly Val Pro Ala Gly Gly Val Pro Ala
        530                 535                 540

Gly Gly Val Pro Ala Ile Gly Val Pro Ala Gly Gly Pro Glu Ala Gly
545                 550                 555                 560

Leu Gly Glu Tyr Leu Phe Glu Arg Leu Thr Leu Lys His Asp
                565                 570

<210> SEQ ID NO 19
<211> LENGTH: 66
<212> TYPE: DNA
<213> ORGANISM: Artificial Sequence
<220> FEATURE:
<223> OTHER INFORMATION: oligonucleotide

<400> SEQUENCE: 19
ctagaaataa ttttgtttaa cttttaagaag gaggagtaca tatgggctac tgataatgat     60
cttcag                                                                 66

<210> SEQ ID NO 20
<211> LENGTH: 66
<212> TYPE: DNA
<213> ORGANISM: Artificial Sequence
<220> FEATURE:
<223> OTHER INFORMATION: oligonucleotide

<400> SEQUENCE: 20
gatcctgaag atcattatca gtagcccata tgtactcctc cttcttaaag ttaaacaaaa     60
ttattt                                                                 66

```
<210> SEQ ID NO 21
<211> LENGTH: 40
<212> TYPE: DNA
<213> ORGANISM: Artificial Sequence
<220> FEATURE:
<223> OTHER INFORMATION: forward primer

<400> SEQUENCE: 21
aaaggatccc cctactggta atgctcttca gtctagagat                              40

<210> SEQ ID NO 22
<211> LENGTH: 40
<212> TYPE: DNA
<213> ORGANISM: Artificial Sequence
<220> FEATURE:
<223> OTHER INFORMATION: reverse primer

<400> SEQUENCE: 22
cacgaccaac ggctactgat agtgatcttc agctagcgat                              40

<210> SEQ ID NO 23
<211> LENGTH: 4
<212> TYPE: PRT
<213> ORGANISM: Artificial Sequence
<220> FEATURE:
<223> OTHER INFORMATION: Elastin-based peptide

<400> SEQUENCE: 23

Val Pro Gly Gly
1

<210> SEQ ID NO 24
<211> LENGTH: 5
<212> TYPE: PRT
<213> ORGANISM: Artificial Sequence
<220> FEATURE:
<223> OTHER INFORMATION: Elastin-based peptide

<400> SEQUENCE: 24

Val Pro Gly Val Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Elastin-based Peptide

<400> SEQUENCE: 25

Ala Pro Gly Val Gly Val
1               5

<210> SEQ ID NO 26
<211> LENGTH: 5
<212> TYPE: PRT
<213> ORGANISM: Artificial Sequence
<220> FEATURE:
<223> OTHER INFORMATION: Elastin-based Peptide
<220> FEATURE:
<221> NAME/KEY: MISC_FEATURE
<222> LOCATION: (3)..(3)
<223> OTHER INFORMATION: A or G
<220> FEATURE:
<221> NAME/KEY: MISC_FEATURE
<222> LOCATION: (4)..(4)
<223> OTHER INFORMATION: Any canonical amino acid other than proline

<400> SEQUENCE: 26
```

```
Val Pro Xaa Xaa Gly
1               5

<210> SEQ ID NO 27
<211> LENGTH: 30
<212> TYPE: PRT
<213> ORGANISM: Artificial Sequence
<220> FEATURE:
<223> OTHER INFORMATION: Elastin-based Peptide
<220> FEATURE:
<221> NAME/KEY: MISC_FEATURE
<222> LOCATION: (4)..(4)
<223> OTHER INFORMATION: Any canonical amino acid other than proline
<220> FEATURE:
<221> NAME/KEY: MISC_FEATURE
<222> LOCATION: (9)..(9)
<223> OTHER INFORMATION: Any canonical amino acid other than proline
<220> FEATURE:
<221> NAME/KEY: MISC_FEATURE
<222> LOCATION: (14)..(14)
<223> OTHER INFORMATION: Any canonical amino acid other than proline
<220> FEATURE:
<221> NAME/KEY: MISC_FEATURE
<222> LOCATION: (19)..(19)
<223> OTHER INFORMATION: Any canonical amino acid other than proline
<220> FEATURE:
<221> NAME/KEY: MISC_FEATURE
<222> LOCATION: (24)..(24)
<223> OTHER INFORMATION: Any canonical amino acid other than proline
<220> FEATURE:
<221> NAME/KEY: misc_feature
<222> LOCATION: (29)..(29)
<223> OTHER INFORMATION: Xaa can be any naturally occurring amino acid

<400> SEQUENCE: 27

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Elastin-based Peptide
<220> FEATURE:
<221> NAME/KEY: MISC_FEATURE
<222> LOCATION: (4)..(4)
<223> OTHER INFORMATION: Any canonical amino acid other than proline
<220> FEATURE:
<221> NAME/KEY: MISC_FEATURE
<222> LOCATION: (9)..(9)
<223> OTHER INFORMATION: Any canonical amino acid other than proline
<220> FEATURE:
<221> NAME/KEY: MISC_FEATURE
<222> LOCATION: (14)..(14)
<223> OTHER INFORMATION: Any canonical amino acid other than proline
<220> FEATURE:
<221> NAME/KEY: MISC_FEATURE
<222> LOCATION: (19)..(19)
<223> OTHER INFORMATION: Any canonical amino acid other than proline
<220> FEATURE:
<221> NAME/KEY: MISC_FEATURE
<222> LOCATION: (24)..(24)
<223> OTHER INFORMATION: Any canonical amino acid other than proline
<220> FEATURE:
<221> NAME/KEY: misc_feature
<222> LOCATION: (29)..(29)
<223> OTHER INFORMATION: Xaa can be any naturally occurring amino acid

<400> SEQUENCE: 28

Val Pro Ala Xaa Gly Val Pro Ala Xaa Gly Val Pro Ala Xaa Gly Val
```

```
1               5                   10                  15
Pro Ala Xaa Gly Val Pro Ala Xaa Gly Val Pro Ala Xaa Gly
            20                  25                  30
```